US007161062B2

(12) United States Patent
Ffrench-Constant et al.

(10) Patent No.: US 7,161,062 B2
(45) Date of Patent: Jan. 9, 2007

(54) **DNA SEQUENCES FROM *PHOTORHABDUS LUMINESCENS***

(75) Inventors: Richard H. Ffrench-Constant, Bath (GB); David J. Bowen, Oregon, WI (US); Thomas A. Rocheleau, Madison, WI (US); Nicholas R. Waterfield, Bath (GB)

(73) Assignee: Wisconsin Alumni Research Foundation, Madison, WI (US)

( * ) Notice: Subject to any disclaimer, the term of this patent is extended or adjusted under 35 U.S.C. 154(b) by 392 days.

(21) Appl. No.: 10/647,956

(22) Filed: Aug. 26, 2003

(65) Prior Publication Data

US 2005/0251878 A1 Nov. 10, 2005

Related U.S. Application Data

(62) Division of application No. 09/817,514, filed on Mar. 26, 2001, now Pat. No. 6,639,129.

(60) Provisional application No. 60/191,806, filed on Mar. 24, 2000.

(51) Int. Cl.
| | |
|---|---|
| *C12N 15/00* | (2006.01) |
| *C12N 15/09* | (2006.01) |
| *C12N 15/31* | (2006.01) |
| *C12N 15/82* | (2006.01) |
| *A01H 5/00* | (2006.01) |
| *A01H 5/10* | (2006.01) |

(52) U.S. Cl. ...................... 800/279; 800/278; 800/298; 800/295; 800/320.1; 800/317; 800/302; 536/23.7; 536/23.1; 435/468; 435/419

(58) Field of Classification Search ................ 800/288, 800/278, 279, 320, 317, 298, 295, 320.1, 800/302; 536/23.7, 23.1; 435/419, 468
See application file for complete search history.

(56) References Cited

U.S. PATENT DOCUMENTS 6,281,413 B1 * 8/2001 Kramer et al. .............. 800/302

FOREIGN PATENT DOCUMENTS

| | | |
|---|---|---|
| WO | WO98/08932 | 3/1998 |
| WO | WO01/11029 | 2/2001 |

OTHER PUBLICATIONS

Morgan, J. Alun et al., "Cloning and expression of Insecticidal toxin genes from *Xenorhabdus* species", SIP 1999 Program & Abstracts, XXXII Meeting, University of California at Irvine, Aug. 22-27, 1999.

Morgan, J. Alun W., et al. Sequence Analysis of Insecticidal Genes from *Xenorhabdus nematophilus* PMF 1296, Applied and Enviornmental Microbiology, 67:2062-2069 (May 2001).

* cited by examiner

*Primary Examiner*—Medina A. Ibrahim
(74) *Attorney, Agent, or Firm*—Donald Stuart

(57) ABSTRACT

Nucleotide sequences for two genes, tcdB and tccC2, from the tcd genomic region of *Photorhabdus luminescens* W-14 are useful in heterologous expression of orally active insect toxins.

11 Claims, No Drawings

DNA SEQUENCES FROM *PHOTORHABDUS LUMINESCENS*

RELATED APPLICATIONS

This application is a divisional of U.S. Ser. No. 09/817,514, filed Mar. 26, 2001, now U.S. Pat. No. 6,639,129, which claims priority from United States Provisional Patent Application Ser. No. U.S. 60/191,806 filed on Mar. 24, 2000.

BACKGROUND OF THE INVENTION

As reported in WO98/08932, protein toxins from the genus *Photorhabdus* have been shown to have oral toxicity against insects. The toxin complex produced by *Photorhabdus luminescens* (W-14), for example, has been shown to contain ten to fourteen proteins, and it is known that these are produced by expression of genes from four distinct genomic regions: tca, tcb, tcc, and tcd. WO98/08932 discloses nucleotide sequences for many of the native toxin genes.

Of the separate toxins isolated from *Photorhabdus luminescens* (W-14), those designated Toxin A and Toxin B have been the subject of focused investigation for their activity against target insect species of interest, for example corn rootworm. Toxin A is comprised of two different subunits. The native gene tcda (SEQ ID NO:1) encodes protoxin TcdA (see SEQ ID NO:1). As determined by mass spectrometry, TcdA is processed by one or more proteases to provide Toxin A. More specifically, TcdA is an approximately 282.9 kDA protein (2516 aa) that is processed to provide TcdAii, an approximately 208.2 kDA (1849 aa) protein encoded by nucleotides 265-5811 of SEQ ID NO:1, and TcdAiii, an approximately 63.5 kDA (579 aa) protein encoded by nucleotides 5812-7551 of SEQ ID NO:1.

WO 01/11029 discloses nucleotide sequences that encode TcdA and TcbA and have base compositions that have been altered from that of the native genes to make them more similar to plant genes. Also disclosed are transgenic plants that express Toxin A and Toxin B.

We have observed that heterologous expression of Toxin A does not afford the level of oral toxicity to insects that is observed for the native toxin. It would be very valuable if means could be found to enhance the level of toxicity of heterologously expressed Toxin A.

SUMMARY OF THE INVENTION

The present invention provides nucleotide sequences for two genes, tcdB and tccC2, from the tcd genomic region of *Photorhabdus luminescens* W-14. These sequences were not previously known. We have discovered that coexpression of tcdB and tccC2 with tcdA in heterologous hosts results in enhanced levels of oral insect toxicity compared to that obtained when tcdA is expressed alone in such heterologous hosts. Coexpression of tcdB and tccC2 with tcdA or tcbA, or with any other functionally equivalent toxin gene in the same family as tcdA and tcbA, to provide enhanced oral insect activity falls within the scope of the invention.

Summary of the Sequences

SEQ ID NO: 1 is the DNA sequence for tcdA from *Photorhabdus luminescens* W-14.

SEQ ID NO: 2 is the amino acid sequence for TcdA from *Photorhabdus luminescens* W-14.

SEQ ID NO: 3 is the DNA sequence for tcdB from *Photorhabdus luminescens* W-14.

SEQ ID NO: 4 is the amino acid sequence for TcdB from *Photorhabdus luminescens* W-14.

SEQ ID NO: 5 is the DNA sequence for tccC2 from *Photorhabdus luminescens* W-14.

SEQ ID NO: 6 is the amino acid sequence for TccC2 from from *Photorhabdus luminescens* W-14.

SEQ ID NO: 7 is the DNA sequence for tcbA from from *Photorhabdus luminescens* W-14.

SEQ ID NO: 8 is the amino acid sequence for TcbA from *Photorhabdus luminescens* W-14.

DETAILED DESCRIPTION OF THE INVENTION

It is preferred for the nucleic acids according to the invention to comprise at least one sequence chosen from
  (a) the sequences according to SEQ ID NOS: 3 and 5.
  (b) at least 14 base pairs-long partial sequences of the sequences defined under (a),
  (c) sequences that hybridize with the sequences defined under (a),
  (d) sequences that are at least 70%, preferably 80% and even more preferred, 90% identical to the sequences defined under (a),
  (e) sequences that are at least 70%, preferably 80% and even more preferred, 90% similar to the sequences defined under (a),
  (f) sequences that complement the sequences defined under (a), and
  (g) sequences that due to the degeneracy of the genetic code, code for the same amino acid sequence as (i.e. are "isocoding" with) the sequences defined under (a) through (e).

The expression "hybridize" as used herein refers to hybridization under the following specified conditions: 5×SSC; blocking reagent (Roche Diagnostics Inc., Mannheim, Germany), 1%; N-lauroyl-sarcosine, 0.1%; SDS (sodium-dodecyl sulfate) 0.02%; hybridization temperature: 60° C.; first wash step: 2×SSC at 60° C.; second wash step: 2×SSC at 60° C.; preferred second wash step: 0.5×SSC at 60° C.; especially preferred second wash step: 0.2×SSC at 60° C.

"Identity" and "similarity" are scored by the GAP algorithm using the Blosum 62 protein scoring matrix (Wisconsin Package Version 9.0, Genetics Computer Group (GCG), Madison, Wis.).

Expression of the Nucleotide Sequences in Heterologous Microbial Hosts

As biological insect control agents, the insecticidal toxins are produced by expression of the nucleotide sequences in heterologous host cells capable of expressing the nucleotide sequences. In a first embodiment, additional copies of one or more of the nucleotide sequences are added to *Xenorhabdus nematophilus, Xenorhabdus poinarii*, or *Photorhabdus luminescens* cells either by insertion into the chromosome or by introduction of extrachromosomally replicating molecules containing the nucleotide sequences.

In another embodiment, at least one of the nucleotide sequences of the invention is inserted into an appropriate expression cassette, comprising a promoter and termination signals. Expression of the nucleotide sequence is constitutive, or an inducible promoter responding to various types of stimuli to initiate transcription is used. In a preferred embodiment, the cell in which the toxin is expressed is a microorganism, such as a virus, a bacteria, or a fungus. In a preferred embodiment, a virus, such as a baculovirus, contains a nucleotide sequence of the invention in its genome and expresses large amounts of the corresponding insecticidal toxin after infection of appropriate eukaryotic cells that are suitable for virus replication and expression of the nucleotide sequence. The insecticidal toxin thus produced is used as an insecticidal agent. Alternatively, baculoviruses engineered to include the nucleotide sequence are used to infect insects in-vivo and kill them either by expression of the insecticidal toxin or by a combination of viral infection and expression of the insecticidal toxin.

Bacterial cells are also hosts for the expression of the nucleotide sequences of the invention. In a preferred embodiment, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera *Agrobacterium, Alcaligenes, Azospiriilum, Azotobacter, Bacillus, Ciavibacter, Enterobacter, Erwinia, Flavobacter, Klebsielia, Pseudomonas, Rhizobium, Serratia, Streptomyces* and *Xanthomonas*. Symbiotic fungi, such as *Trichoderma* and *Gliocladium* are also possible hosts for expression of the inventive nucleotide sequences for the same purpose.

Techniques for these genetic manipulations are specific for the different available hosts and are known in the art. For example, the expression vectors pKK223-3 and pKK223-2 can be used to express heterologous genes in *E. coli*, either in transcriptional or translational fusion, behind the tac or trc promoter. For the expression of operons encoding multiple ORFS, the simplest procedure is to insert the operon into a vector such as pKK2233 in transcriptional fusion, allowing the cognate ribosome binding site of the heterologous genes to be used. Techniques for overexpression in gram-positive species such as *Bacillus* are also known in the art and can be used in the context of this invention (Quax et al. In.: Industrial Microorganisms: Basic and Applied Molecular Genetics, Eds. Baltz et al., American Society for Microbiology, Washington (1993)). Alternate systems for overexpression rely for example, on yeast vectors and include the use of *Pichia, Saccharomyces* and *Kluyveromyces* (Sreekrishna, In: industrial microorganisms: basic and applied molecular genetics, Baltz, Hegeman, and Skatrud eds., American Society for Microbiology, Washington (1993); Dequin & Barre, Biotechnology 12:173–177 (1994); van den Berg et al., Biotechnology 8:135–139 (1990)).

Expression of the Nucleotide Sequences in Plant Tissue

In a particularly preferred embodiment, at least one of the insecticidal toxins of the invention is expressed in a higher organism, e.g., a plant. In this case, transgenic plants expressing effective amounts of the toxins protect themselves from insect pests. When the insect starts feeding on such a transgenic plant, it also ingests the expressed toxins. This will deter the insect from further biting into the plant tissue or may even harm or kill the insect. A nucleotide sequence of the present invention is inserted into an expression cassette, which is then preferably stably integrated in the genome of said plant, In another preferred embodiment, the nucleotide sequence is included in a non-pathogenic self-replicating virus. Plants transformed in accordance with the present invention may be monocots or dicots and include, but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugarbeet, sunflower, rapeseed, clover, tobacco, carrot, cotton, alfalfa, rice, potato, eggplant, cucumber, Arabidopsis, and woody plants such as coniferous and deciduous trees.

Once a desired nucleotide sequence has been transformed into a particular plant species, it may be propagated in that species or moved into other varieties of the same species, particularly including commercial varieties, using traditional breeding techniques.

A nucleotide sequence of this invention is preferably expressed in transgenic plants, thus causing the biosynthesis of the corresponding toxin in the transgenic plants. In this way, transgenic plants with enhanced resistance to insects are generated. For their expression in transgenic plants, the nucleotide sequences of the invention may require modification and optimization. Although in many cases genes from microbial organisms can be expressed in plants at high levels without modification, low expression in transgenic plants may result from microbial nucleotide sequences having codons that are not preferred in plants. It is known in the art that all organisms have specific preferences for codon usage, and the codons of the nucleotide sequences described in this invention can be changed to conform with plant preferences, while maintaining the amino acids encoded thereby. Furthermore, high expression in plants is best achieved from coding sequences that have at least about 35% GC content, preferably more than about 45%, more preferably more than about 50%, and most preferably more than about 60%. Microbial nucleotide sequences which have low GC contents may express poorly in plants due to the existence of ATTTA motifs which may destabilize messages, and AATAAA motifs which may cause inappropriate polyadenylation. Although preferred gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17:477–498 (1989)). In addition, the nucleotide sequences are screened for the existence of illegitimate splice sites that may cause message truncation. All changes required to be made within the nucleotide sequences such as those described above are made using well known techniques of site directed mutagenesis, PCR, and synthetic gene construction.

For efficient initiation of translation, sequences adjacent to the initiating methionine may require modification. For example, they can be modified by the inclusion of sequences known to be effective in plants. Joshi has suggested an appropriate consensus for plants (NAR 15:6643–6653 (1987)) and Clontech suggests a further consensus translation initiator (1993/1994 catalog, page 210). These consensuses are suitable for use with the nucleotide sequences of this invention. The sequences are incorporated into constructions comprising the nucleotide sequences, up to and including the ATG (whilst leaving the second amino acid unmodified), or alternatively up to and including the GTC subsequent to the ATG (with the possibility of modifying the second amino acid of the transgene).

Expression of the nucleotide sequences in transgenic plants is driven by promoters shown to be functional in plants. The choice of promoter will vary depending on the temporal and spatial requirements for expression, and also depending on the target species. Thus, expression of the nucleotide sequences of this invention in leaves, in ears, in inflorescences (e.g. spikes, panicles, cobs, etc.), in roots, and/or seedlings is preferred. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

Preferred promoters that are expressed constitutively include promoters from genes encoding actin or ubiquitin and the CAMV 35S and 19S promoters. The nucleotide sequences of this invention can also be expressed under the regulation of promoters that are chemically regulated. This enables the insecticidal toxins to be synthesized only when the crop plants are treated with the inducing chemicals.

A preferred category of promoters is that which is wound inducible. Numerous promoters have been described which are expressed at wound sites and also at the sites of phytopathogen infection. Ideally, such a promoter should only be active locally at the sites of infection, and in this way the insecticidal toxins only accumulate in cells which need to synthesize the insecticidal toxins to kill the invading insect pest. Preferred promoters of this kind include those described by Stanford et al. Mol. Gen. Genet. 215:200–208 (1989), Xu et al. Plant Molec. Biol. 22:573–588 (1993), Logemann et al. Plant Cell 1: 151–158 (1989), Rohrmeier & Lehle, Plant Molec. Biol. 22:783–792 (1993), Firek et al. Plant Molec. Biol. 22: 129–142 (1993), and Warner et al. Plant J. 3:191–201 (1993).

Especially preferred embodiments of the invention are transgenic plants expressing at least one of the nucleotide sequences of the invention in a root-preferred or root-specific fashion. Further preferred embodiments are transgenic plants expressing the nucleotide sequences in a wound-inducible or pathogen infection-inducible manner.

In addition to the selection of a suitable promoter, constructions for expression of an insecticidal toxin in plants require an appropriate transcription terminator to be attached downstream of the heterologous nucleotide sequence. Several such terminators are available and known in the art (e.g. tml from *Agrobacterium*, E9 from rbcs). Any available terminator known to function in plants can be used in the context of this invention.

Numerous other sequences can be incorporated into expression cassettes described in this invention. These include sequences which have been shown to enhance expression such as intron sequences (e.g. from Adhl and bronzel) and viral leader sequences (e.g. from TMV, MCMV and AMV).

It may be preferable to target expression of the nucleotide sequences of the present invention to different cellular localizations in the plant. In some cases, localization in the cytosol may be desirable, whereas in other cases, localization in some subcellular organelle may be preferred. Subcellular localization of transgene encoded enzymes is undertaken using techniques well known in the art Typically, the DNA encoding the target peptide from a known organelle-targeted gene product is manipulated and fused upstream of the nucleotide sequence. Many such target sequences are known for the chloroplast and their functioning in heterologous constructions has been shown. The expression of the nucleotide sequences of the present invention is also targeted to the endoplasmic reticulum or to the vacuoles of the host cells. Techniques to achieve this are well-known in the art.

Vectors suitable for plant transformation are described elsewhere in this specification. For *Agrobacterium* -mediated transformation, binary vectors or vectors carrying at least one T-DNA border sequence are suitable, whereas for direct gene transfer any vector is suitable and linear DNA containing only the construction of interest may be preferred. In the case of direct gene transfer, transformation with a single DNA species or co-transformation can be used (Schocher et al. Biotechnology 4:1093–1096 (1986)). For both direct gene transfer and Agrobacterium-mediated transfer, transformation is usually (but not necessarily) undertaken with a selectable or screenable marker which may provide resistance to an antibiotic (kanamycin, hygromycin or methotrexate) or a herbicide (Basta). Examples of such markers are neomycin phosphotransferase, hygromycin phosphotransferase, dihydrofolate reductase, phosphinothricin acetyltransferase, 2,2-dichloroproprionic acid dehalogenase, acetohydroxyacid synthase, 5-enolpyruvyl-shikimate-phosphate synthase, haloarylnitrilase, protoporhyrinogen oxidase, acetyl-coenzyme A carboxylase, dihydropteroate synthase, chloramphenicol acetyl transferase, and glucuronidase. The choice of selectable or screenable marker for plant transformation is not, however, critical to the invention.

The recombinant DNA described above can be introduced into the plant cell in a number of art-recognized ways. Those skilled in the art will appreciate that the choice of method might depend on the type of plant targeted for transformation. Suitable methods of transforming plant cells include microinjection (Crossway et al., BioTechniques 4.,320–334 (1986)), electroporation (Riggs et al., Proc. Natl. Acad, Sci. USA 83.,5602–5606 (1986), *Agrobacterium* -mediated transformation (Hinchee et al., Biotechnology 6:915–921 (1988); See also, lshida et al., Nature Biotechnology 14:745–750 (June 1996) (for maize transformation), direct gene transfer (Paszkowski et al., EMBO J. 3.2717–2722 (1984); Hayashimoto et al., Plant Physiol 93.857–863 (1990) (rice), and ballistic particle acceleration using devices available from Agracetus, Inc., Madison, Wis. and Dupont, Inc., Wilmington, Del. (see, for example, Sanford et al., U.S. Pat. No. 4,945,050; and McCabe et al., Biotechnology 6.923–926 (1988)). See also, Weissinger et al., Annual Rev Genet. 22.–421–477 (1988); Sanford et al., Particulate Science and Technology 5.27–37 (1987)(onion); Svab et al., Proc. Natl. Acad. Sci. USA 87.- 8526–8530 (1990) (tobacco chloroplast); Christou et al., Plant Physiol 87,671–674 (1988) (soybean); McCabe et al., BioTechnology 6.923–926 (1988)(soybean); Klein et al., Proc. Natl. Acad. Sci. USA, 85:4305–4309 (1988) (maize); Klein et al., BioTechnology 6.,559–563 (1988) (maize); Klein et al., Plant PhysioL 91.,440–444 (1988) (maize); Fromm et al., BioTechnology 8:833–839 (1990); and Gordon-Kamm et al., Plant Cell 2: 603–618 (1990) (maize); Koziel et al., Biotechnology 1 1: 194–200 (1993) (maize); Shimamoto et al., Nature 338: 274–277 (1989) (rice); Christou et al., Biotechnology 9: 957–962 (1991) (rice); Datta et al., Bio-Technology 8.736–740 (1990) (rice); European Patent Application EP 0 332 581 (orchardgrass and other Pooideae); Vasil et al., Biotechnology 1 1: 1553–1558 (1993) (wheat); Weeks et al., Plant Physiol. 102:1077–1084 (1993) (wheat); wan et al., Plant Physiol. 104:37–48 (1994) (barley); Jahne et al., Theor. Appl. Genet. 89:525–533 (1994) (barley); Umbeck et al., BioTechnology 5:263–266 (1987) (cotton); Casas et al., Proc. Natl. Acad. Sci. USA 90:11212–11216 (December 1993) (sorghum); Somers et al., BioTechnology 10:1 589–1594 (December 1992) (oat); Torbert et al., Plant Cell Reports 14:635–640 (1995) (oat);

Weeks et al., Plant Physiol. 102:1077–1084 (1993) (wheat); Chang et al., WO 94/13822 (wheat) and Nehra et al., The Plant Journal 5:285–297 (1994) (wheat). A particularly preferred set of embodiments for the introduction of recombinant DNA molecules into maize by microprojectile bombardment can be found in Koziel et al., Biotechnology 11: 194–200(1993), Hill et al., Euphytica 85:119–123 (1995) and Koziel et al., Annals of the New York Academy of Sciences 792:164–171 (1996). An additional preferred embodiment is the protoplast transformation method for maize as disclosed in EP 0 292 435. Transformation of plants can be undertaken with a single DNA species or multiple DNA species (i.e. co-transformation).

In another preferred embodiment, a nucleotide sequence of the present invention is directly transformed into the plastid genome. A major advantage of plastid transformation is that plastids are generally capable of expressing bacterial genes without substantial modification, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) Proc. Natl. Acad. Sci. USA 91, 7301–7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rpsl2 genes conferring resistance to spectinomycin and/or streptomycin are utilized as selectable markers for transformation (Svab, Z., Hajdukiewicz, P., and Maliga, P. (1990) Proc. Nati. Acad. Sci. USA 87, 8526–8530; Staub, J. M., and Maliga, P. (1992) Plant Cell 4, 39–45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) EMBO J. 12, 601–606). Substantial increases in transformation frequency are obtained by replacement of the recessive RRNA or r-protein antibiotic resistance genes with a dominant selectable marker, the bacterial aada gene encoding the spectinomycin-detoxifying enzyme aminoglycoside-3' adenyltransferase (Svab, Z., and Maliga, P. (1993) Proc. Natl. Acad. Sci. USA 90, 913–917). Previously, this marker had been used successfully for high-frequency transformation of the plastid genome of the green alga *Chlamydomonas reinhardtii* (Goldschmidt-Clermont, M. (1991) Nucl. Acids Res. 19: 4083–4089). Other selectable markers useful for plastid transformation are known in the art and encompassed within the scope of the invention. Typically, approximately 15–20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleotide sequence of the present invention is inserted into a plastid targeting vector and transformed into the plastid genome of a desired plant host. Plants homoplastic for plastid genomes containing a nucleotide sequence of the present invention are obtained, and are preferentially capable of high expression of the nucleotide sequence.

Provisional Patent Application Ser. No. U.S. 60/191,806 filed Mar. 24, 2000, is hereby incorporated by reference.

We claim:

1. An isolated nucleic acid that encodes SEQ ID NO:6.

2. The isolated nucleic acid of claim 1 comprising SEQ ID NO:5.

3. A transgenic monocot cell having a genome comprising an isolated nucleic acid that encodes the protein of SEQ ID NO:6.

4. A transgenic dicot cell having a genome comprising a nucleic acid sequence that encodes the protein of SEQ ID NO:6.

5. A transgenic plant with a genome comprising a nucleic acid nucleic acid sequence that encodes the protein of SEQ ID NO:6.

6. A transgenic plant of claim 5 wherein the plant is rice.

7. A transgenic plant of claim 5 wherein the plant is maize.

8. A transgenic plant of claim 5 wherein the plant is tobacco.

9. A transgenic plant of claim 5 wherein the plant is cotton.

10. Transgenic seed of a transgenic plant of claim 5.

11. Transgenic progeny of the seed of claim 10.

* * * * *

SEQUENCE LISTING

<160> NUMBER OF SEQ ID NOS: 8

<210> SEQ ID NO 1
<211> LENGTH: 7551
<212> TYPE: DNA
<213> ORGANISM: Photorhabdus luminescens

<400> SEQUENCE: 1

```
atgaacgagt ctgtaaaaga gatacctgat gtattaaaaa gccagtgtgg ttttaattgt      60
ctgacagata ttagccacag ctcttttaat gaatttcgcc agcaagtatc tgagcacctc     120
tcctggtccg aaacacacga cttatatcat gatgcacaac aggcacaaaa ggataatcgc     180
ctgtatgaag cgcgtattct caaacgcgcc aatccccaat tacaaaatgc ggtgcatctt     240
gccattctcg ctcccaatgc tgaactgata ggctataaca atcaatttag cggtagagcc     300
agtcaatatg ttgcgccggg taccgtttct tccatgttct ccccgccgc ttatttgact      360 gaactttatc gtgaagcacg caatttacac gcaagtgact ccgtttatta tctggatacc     420
cgccgcccag atctcaaatc aatggcgctc agtcagcaaa atatggatat agaattatcc     480
acactctctt tgtccaatga gctgttattg gaaagcatta aaactgaatc taaactggaa     540
aactatacta aagtgatgga aatgctctcc actttccgtc cttccggcgc aacgccttat     600
catgatgctt atgaaaatgt gcgtgaagtt atccagctac aagatcctgg acttgagcaa     660
```

-continued

```
ctcaatgcat caccggcaat tgccggggtg atgcatcaag cctccctatt gggtattaac    720
gcttcaatct cgcctgagct atttaatatt ctgacggagg agattaccga aggtaatgct    780
gaggaacttt ataagaaaaa ttttggtaat atcgaaccgg cctcattggc tatgccggaa    840
taccttaaac gttattataa tttaagcgat gaagaactta gtcagtttat tggtaaagcc    900
agcaattttg gtcaacagga atatagtaat aaccaactta ttactccggt agtcaacagc    960
agtgatggca cggttaaggt atatcggatc acccgcgaat atacaaccaa tgcttatcaa   1020
atggatgtgg agctatttcc cttcggtggt gagaattatc ggttagatta taaattcaaa   1080
aattttata atgcctctta tttatccatc aagttaaatg ataaagaga acttgttcga    1140
actgaaggcg ctcctcaagt caatatagaa tactccgcaa atatcacatt aaataccgct   1200
gatatcagtc aaccttttga aattggcctg acacgagtac ttccttccgg ttcttgggca   1260
tatgccgccg caaaatttac cgttgaagag tataaccaat actcttttct gctaaaactt   1320
aacaaggcta ttcgtctatc acgtgcgaca gaattgtcac ccacgattct ggaaggcatt   1380
gtgcgcagtg ttaatctaca actggatatc aacacagacg tattaggtaa agttttctg   1440
actaaatatt atatgcagcg ttatgctatt catgctgaaa ctgccctgat actatgcaac   1500
gcgcctattt cacaacgttc atatgataat caacctagcc aatttgatcg cctgtttaat   1560
acgccattac tgaacggaca atattttct accggcgatg aggagattga tttaaattca   1620
ggtagcaccg gcgattggcg aaaaaccata cttaagcgtg catttaatat tgatgatgtc   1680
tcgctcttcc gcctgcttaa aattaccgac catgataata aagatggaaa aattaaaaat   1740
aacctaaaga atcttccaa tttatatatt ggaaaattac tggcagatat tcatcaatta   1800
accattgatg aactggattt attactgatt gccgtaggtg aaggaaaac taatttatcc    1860
gctatcagtg ataagcaatt ggctaccctg atcagaaaac tcaatactat taccagctgg   1920
ctacatacac agaagtggag tgtattccag ctatttatca tgacctccac cagctataac   1980
aaaacgctaa cgcctgaaat taagaatttg ctggataccg tctaccacgg tttacaaggt   2040
tttgataaag acaaagcaga tttgctacat gtcatggcgc cctatattgc ggccaccttg   2100
caattatcat cggaaaatgt cgcccactcg gtactccttt gggcagataa gttacagccc   2160
ggcgacggcg caatgacagc agaaaaattc tgggactggt tgaatactaa gtatacgccg   2220
ggttcatcgg aagccgtaga acgcaggaa catatcgttc agtattgtca ggctctggca   2280
caattggaaa tggtttacca ttccaccggc atcaacgaaa acgccttccg tctatttgtg   2340
acaaaaccag agatgtttgg cgctgcaact ggagcagcgc ccgcgcatga tgccctttca   2400
ctgattatgc tgcacgtttt tgcggattgg gtgaacgcac taggcaaaaa agcgtcctcg   2460
gtgctagcgg catttgaagc taactcgtta acggcagaac aactggctga tgccatgaat   2520
cttgatgcta atttgctgtt gcaagccagt attcaagcac aaaatcatca acatcttccc   2580
ccagtaactc cagaaaatgc gttctcctgt tggacatcta tcaatactat cctgcaatgg   2640
gttaatgtcg cacaacaatt gaatgtcgcc ccacagggcg tttccgcttt ggtcgggctg   2700
gattatattc aatcaatgaa agagacaccg acctatgccc agtgggaaaa cgcggcaggc   2760
gtattaaccg ccgggttgaa ttcacaacag gctaatacat tacacgcttt tctggatgaa   2820
tctcgcagtg ccgcattaag cacctactat atccgtcaag tcgccaaggc agcggcggct   2880
attaaaagcc gtgatgactt gtatcaatac ttactgattg ataatcaggt ttctgcggca   2940
ataaaaacca cccggatcgc cgaagccatt gccagtattc aactgtacgt caaccgggca   3000
```

-continued

```
ttggaaaatg tggaagaaaa tgccaattcg ggggttatca gccgccaatt ctttatcgac    3060
tgggacaaat acaataaacg ctacagcact tgggcgggtg tttctcaatt agtttactac    3120
ccggaaaact atattgatcc gaccatgcgt atcggacaaa ccaaaatgat ggacgcatta    3180
ctgcaatccg tcagccaaag ccaattaaac gccgataccg tcgaagatgc ctttatgtct    3240
tatctgacat cgtttgaaca agtggctaat cttaaagtta ttagcgcata tcacgataat    3300
attaataacg atcaagggct gacctatttt atcggactca gtgaaactga tgccggtgaa    3360
tattattggc gcagtgtcga tcacagtaaa ttcaacgacg gtaaattcgc ggctaatgcc    3420
tggagtgaat ggcataaaat tgattgtcca attaaccctt ataaaagcac tatccgtcca    3480
gtgatatata aatcccgcct gtatctgctc tggttggaac aaaaggagat caccaaacag    3540
acaggaaata gtaagatgg ctatcaaact gaaacggatt atcgttatga actaaaattg    3600
gcgcatatcc gctatgatgg cacttggaat acgccaatca cctttgatgt caataaaaaa    3660
atatccgagc taaaactgga aaaaataga gcgcccggac tctattgtgc cggttatcaa    3720
ggtgaagata cgttgctggt gatgttttat aaccaacaag acacactaga tagttataaa    3780
aacgcttcaa tgcaaggact atatatcttt gctgatatgg catccaaaga tatgacccca    3840
gaacagagca atgtttatcg ggataatagc tatcaacaat ttgataccaa taatgtcaga    3900
agagtgaata accgctatgc agaggattat gagattcctt cctcggtaag tagccgtaaa    3960
gactatggtt ggggagatta ttacctcagc atggtatata acggagatat tccaactatc    4020
aattacaaag ccgcatcaag tgatttaaaa atctatatct caccaaaatt aagaattatt    4080
cataatggat atgaaggaca gaagcgcaat caatgcaatc tgatgaataa atatggcaaa    4140
ctaggtgata aatttattgt ttatactagc ttggggggtca atccaaataa ctcgtcaaat    4200
aagctcatgt tttaccccgt ctatcaatat agcggaaaca ccagtggact caatcaaggg    4260
agactactat tccaccgtga caccacttat ccatctaaag tagaagcttg gattcctgga    4320
gcaaaacgtt ctctaaccaa ccaaaatgcc gccattggtg atgattatgc tacagactct    4380
ctgaataaac cggatgatct taagcaatat atctttatga ctgacagtaa agggactgct    4440
actgatgtct caggcccagt agagattaat actgcaattt ctccagcaaa agttcagata    4500
atagtcaaag cgggtggcaa ggagcaaact tttaccgcag ataaagatgt ctccattcag    4560
ccatcaccta gctttgatga aatgaattat caatttaatg cccttgaaat agacggttct    4620
ggtctgaatt ttattaacaa ctcagccagt attgatgtta cttttaccgc atttgcggag    4680
gatggccgca aactgggtta tgaaagtttc agtattcctg ttaccctcaa ggtaagtacc    4740
gataatgccc tgaccctgca ccataatgaa atggtgcgc aatatatgca atggcaatcc    4800
tatcgtaccc gcctgaatac tctatttgcc cgccagttgg ttgcacgcgc caccaccgga    4860 atcgataaa ttctgagtat ggaaactcag aatattcagg aaccgcagtt aggcaaaggt    4920

ttctatgcta cgttcgtgat acctcctat aacctatcaa ctcatggtga tgaacgttgg    4980

tttaagcttt atatcaaaca tgttgttgat aataattcac atattatcta ttcaggccag    5040
ctaacagata caaatataaa catcacatta tttattctc ttgatgatgt cccattgaat    5100
caagattatc acgccaaggt ttatatgacc ttcaagaaat caccatcaga tggtacctgg    5160
tggggccctc actttgttag agatgataaa ggaatagtaa caataaaccc taaatccatt    5220

ттgaccccaтт ttgagagcgt caatgtcctg aataatatta gtagcgaacc aatggatttc    5280
agcggcgcta acagcctcta tttctgggaa ctgttctact ataccccgat gctggttgct    5340 caacgттттgc tgcatgaaca gaacttcgat gaagccaacc gttggctgaa atatgtctgg    5400
```

-continued

```
agtccatccg gttatattgt ccacggccag attcagaact accagtggaa cgtccgcccg    5460
ttactggaag acaccagttg gaacagtgat cctttggatt ccgtcgatcc tgacgcggta    5520
gcacagcacg atccaatgca ctacaaagtt tcaactttta tgcgtacctt ggatctattg    5580
atagcacgcg gcgaccatgc ttatcgccaa ctggaacgag atacactcaa cgaagcgaag    5640
atgtggtata tgcaagcgct gcatctatta ggtgacaaac cttatctacc gctgagtacg    5700
acatggagtg atccacgact agacagagcc gcggatatca ctacccaaaa tgctcacgac    5760
agcgcaatag tcgctctgcg gcagaatata cctacaccgg cacctttatc attgcgcagc    5820
gctaataccc tgactgatct cttcctgccg caaatcaatg aagtgatgat gaattactgg    5880
cagacattag ctcagagagt atacaatctg cgtcataacc tctctatcga cggccagccg    5940
ttatatctgc caatctatgc cacaccggcc gatccgaaag cgttactcag cgccgccgtt    6000
gccacttctc aaggtggagg caagctaccg gaatcattta tgtccctgtg gcgtttcccg    6060
cacatgctgg aaaatgcgcg cggcatggtt agccagctca cccagttcgg ctccacgtta    6120
caaaatatta tcgaacgtca ggacgcggaa gcgctcaatg cgttattaca aaatcaggcc    6180
gccgagctga tattgactaa cctgagcatt caggacaaaa ccattgaaga attggatgcc    6240
gagaaaacgg tgttggaaaa atccaaagcg ggagcacaat cgcgctttga tagctacggc    6300
aaactgtacg atgagaatat caacgccggt gaaaaccaag ccatgacgct acgagcgtcc    6360
gccgccgggc ttaccacggc agttcaggca tcccgtctgg ccggtgcggc ggctgatctg    6420
gtgcctaaca tcttcggctt tgccggtggc ggcagccgtt gggggctat cgctgaggcg    6480 acaggttatg tgatgaatt ctccgcgaat gttatgaaca ccgaagcgga taaaattagc    6540
caatctgaaa cctaccgtcg tcgccgtcag gagtgggaga tccagcggaa taatgccgaa    6600
gcggaattga agcaaatcga tgctcagctc aaatcactcg ctgtacgccg cgaagccgcc    6660
gtattgcaga aaaccagtct gaaaacccaa caagaacaga cccaatctca attggccttc    6720
ctgcaacgta agttcagcaa tcaggcgtta tacaactggc tgcgtggtcg actggcggcg    6780 attacttcc agttctacga tttggccgtc gcgcgttgcc tgatggcaga acaagcttac    6840
cgttgggaac tcaatgatga ctctgcccgc ttcattaaac cgggcgcctg gcagggaacc    6900
tatgccggtc tgcttgcagg tgaaaccttg atgctgagtc tggcacaaat ggaagacgct    6960
catctgaaac gcgataaacg cgcattagag gttgaacgca cagtatcgct ggccgaagtt    7020
tatgcaggat taccaaaaga taacggtcca ttttccctgg ctcaggaaat tgacaagctg    7080
gtgagtcaag gttcaggcag tgccggcagt ggtaataata atttggcgtt cggcgccggc    7140
acggacacta aaacctcttt gcaggcatca gtttcattcg ctgatttgaa aattcgtgaa    7200
gattacccgg catcgcttgg caaaattcga cgtatcaaac agatcagcgt cactttgccc    7260
gcgctactgg gaccgtatca ggatgtacag gcaatattgt cttacggcga taaagccgga    7320
ttagctaacg gctgtgaagc gctggcagtt tctcacggta tgaatgacag cggccaattc    7380
cagctcgatt tcaacgatgg caaattcctg ccattcgaag catcgccat tgatcaaggc    7440 acgctgacac tgagcttccc aaatgcatct atgccggaga aaggtaaaca agccactatg    7500 ttaaaaccc tgaacgatat cattttgcat attcgctaca ccattaaata a            7551
```

<210> SEQ ID NO 2
<211> LENGTH: 2516
<212> TYPE: PRT
<213> ORGANISM: Photorhabdus luminescens

<400> SEQUENCE: 2

```
Met Asn Glu Ser Val Lys Glu Ile Pro Asp Val Leu Lys Ser Gln Cys
1               5                   10                  15

Gly Phe Asn Cys Leu Thr Asp Ile Ser His Ser Ser Phe Asn Glu Phe
            20                  25                  30

Arg Gln Gln Val Ser Glu His Leu Ser Trp Ser Glu Thr His Asp Leu
        35                  40                  45

Tyr His Asp Ala Gln Gln Ala Gln Lys Asp Asn Arg Leu Tyr Glu Ala
    50                  55                  60

Arg Ile Leu Lys Arg Ala Asn Pro Gln Leu Gln Asn Ala Val His Leu
65                  70                  75                  80

Ala Ile Leu Ala Pro Asn Ala Glu Leu Ile Gly Tyr Asn Asn Gln Phe
                85                  90                  95

Ser Gly Arg Ala Ser Gln Tyr Val Ala Pro Gly Thr Val Ser Ser Met
            100                 105                 110

Phe Ser Pro Ala Ala Tyr Leu Thr Glu Leu Tyr Arg Glu Ala Arg Asn
        115                 120                 125

Leu His Ala Ser Asp Ser Val Tyr Tyr Leu Asp Thr Arg Arg Pro Asp
    130                 135                 140

Leu Lys Ser Met Ala Leu Ser Gln Gln Asn Met Asp Ile Glu Leu Ser
145                 150                 155                 160

Thr Leu Ser Leu Ser Asn Glu Leu Leu Leu Glu Ser Ile Lys Thr Glu
                165                 170                 175

Ser Lys Leu Glu Asn Tyr Thr Lys Val Met Glu Met Leu Ser Thr Phe
            180                 185                 190

Arg Pro Ser Gly Ala Thr Pro Tyr His Asp Ala Tyr Glu Asn Val Arg
        195                 200                 205

Glu Val Ile Gln Leu Gln Asp Pro Gly Leu Glu Gln Leu Asn Ala Ser
    210                 215                 220

Pro Ala Ile Ala Gly Leu Met His Gln Ala Ser Leu Leu Gly Ile Asn
225                 230                 235                 240

Ala Ser Ile Ser Pro Glu Leu Phe Asn Ile Leu Thr Glu Glu Ile Thr
                245                 250                 255

Glu Gly Asn Ala Glu Glu Leu Tyr Lys Lys Asn Phe Gly Asn Ile Glu
            260                 265                 270

Pro Ala Ser Leu Ala Met Pro Glu Tyr Leu Lys Arg Tyr Tyr Asn Leu
        275                 280                 285

Ser Asp Glu Glu Leu Ser Gln Phe Ile Gly Lys Ala Ser Asn Phe Gly
    290                 295                 300

Gln Gln Glu Tyr Ser Asn Asn Gln Leu Ile Thr Pro Val Val Asn Ser
305                 310                 315                 320

Ser Asp Gly Thr Val Lys Val Tyr Arg Ile Thr Arg Glu Tyr Thr Thr
                325                 330                 335

Asn Ala Tyr Gln Met Asp Val Glu Leu Phe Pro Phe Gly Gly Glu Asn
            340                 345                 350

Tyr Arg Leu Asp Tyr Lys Phe Lys Asn Phe Tyr Asn Ala Ser Tyr Leu
        355                 360                 365

Ser Ile Lys Leu Asn Asp Lys Arg Glu Leu Val Arg Thr Glu Gly Ala
    370                 375                 380

Pro Gln Val Asn Ile Glu Tyr Ser Ala Asn Ile Thr Leu Asn Thr Ala
385                 390                 395                 400

Asp Ile Ser Gln Pro Phe Glu Ile Gly Leu Thr Arg Val Leu Pro Ser
                405                 410                 415
```

```
Gly Ser Trp Ala Tyr Ala Ala Lys Phe Thr Val Glu Glu Tyr Asn
        420                 425                 430

Gln Tyr Ser Phe Leu Leu Lys Leu Asn Lys Ala Ile Arg Leu Ser Arg
            435                 440                 445

Ala Thr Glu Leu Ser Pro Thr Ile Leu Glu Gly Ile Val Arg Ser Val
        450                 455                 460

Asn Leu Gln Leu Asp Ile Asn Thr Asp Val Leu Gly Lys Val Phe Leu
465                 470                 475                 480

Thr Lys Tyr Tyr Met Gln Arg Tyr Ala Ile His Ala Glu Thr Ala Leu
            485                 490                 495

Ile Leu Cys Asn Ala Pro Ile Ser Gln Arg Ser Tyr Asp Asn Gln Pro
        500                 505                 510

Ser Gln Phe Asp Arg Leu Phe Asn Thr Pro Leu Leu Asn Gly Gln Tyr
        515                 520                 525

Phe Ser Thr Gly Asp Glu Glu Ile Asp Leu Asn Ser Gly Ser Thr Gly
        530                 535                 540

Asp Trp Arg Lys Thr Ile Leu Lys Arg Ala Phe Asn Ile Asp Asp Val
545                 550                 555                 560

Ser Leu Phe Arg Leu Leu Lys Ile Thr Asp His Asp Asn Lys Asp Gly
            565                 570                 575

Lys Ile Lys Asn Asn Leu Lys Asn Leu Ser Asn Leu Tyr Ile Gly Lys
        580                 585                 590

Leu Leu Ala Asp Ile His Gln Leu Thr Ile Asp Glu Leu Asp Leu Leu
        595                 600                 605

Leu Ile Ala Val Gly Glu Gly Lys Thr Asn Leu Ser Ala Ile Ser Asp
        610                 615                 620

Lys Gln Leu Ala Thr Leu Ile Arg Lys Leu Asn Thr Ile Thr Ser Trp
625                 630                 635                 640

Leu His Thr Gln Lys Trp Ser Val Phe Gln Leu Phe Ile Met Thr Ser
            645                 650                 655

Thr Ser Tyr Asn Lys Thr Leu Thr Pro Glu Ile Lys Asn Leu Leu Asp
        660                 665                 670

Thr Val Tyr His Gly Leu Gln Gly Phe Asp Lys Asp Lys Ala Asp Leu
        675                 680                 685

Leu His Val Met Ala Pro Tyr Ile Ala Ala Thr Leu Gln Leu Ser Ser
        690                 695                 700

Glu Asn Val Ala His Ser Val Leu Leu Trp Ala Asp Lys Leu Gln Pro
705                 710                 715                 720

Gly Asp Gly Ala Met Thr Ala Glu Lys Phe Trp Asp Leu Asn Thr
            725                 730                 735

Lys Tyr Thr Pro Gly Ser Ser Glu Ala Val Glu Thr Gln Glu His Ile
            740                 745                 750

Val Gln Tyr Cys Gln Ala Leu Ala Gln Leu Glu Met Val Tyr His Ser
            755                 760                 765

Thr Gly Ile Asn Glu Asn Ala Phe Arg Leu Phe Val Thr Lys Pro Glu
        770                 775                 780

Met Phe Gly Ala Ala Thr Gly Ala Ala Pro Ala His Asp Ala Leu Ser
785                 790                 795                 800

Leu Ile Met Leu Thr Arg Phe Ala Asp Trp Val Asn Ala Leu Gly Glu
            805                 810                 815

Lys Ala Ser Ser Val Leu Ala Ala Phe Glu Ala Asn Ser Leu Thr Ala
        820                 825                 830
```

```
Glu Gln Leu Ala Asp Ala Met Asn Leu Asp Ala Asn Leu Leu Leu Gln
        835                 840                 845

Ala Ser Ile Gln Ala Gln Asn His Gln His Leu Pro Pro Val Thr Pro
850                 855                 860

Glu Asn Ala Phe Ser Cys Trp Thr Ser Ile Asn Thr Ile Leu Gln Trp
865                 870                 875                 880

Val Asn Val Ala Gln Gln Leu Asn Val Ala Pro Gln Gly Val Ser Ala
                885                 890                 895

Leu Val Gly Leu Asp Tyr Ile Gln Ser Met Lys Glu Thr Pro Thr Tyr
            900                 905                 910

Ala Gln Trp Glu Asn Ala Ala Gly Val Leu Thr Ala Gly Leu Asn Ser
            915                 920                 925

Gln Gln Ala Asn Thr Leu His Ala Phe Leu Asp Glu Ser Arg Ser Ala
        930                 935                 940

Ala Leu Ser Thr Tyr Tyr Ile Arg Gln Val Ala Lys Ala Ala Ala Ala
945                 950                 955                 960

Ile Lys Ser Arg Asp Asp Leu Tyr Gln Tyr Leu Leu Ile Asp Asn Gln
                965                 970                 975

Val Ser Ala Ala Ile Lys Thr Thr Arg Ile Ala Glu Ala Ile Ala Ser
            980                 985                 990

Ile Gln Leu Tyr Val Asn Arg Ala  Leu Glu Asn Val Glu  Glu Asn Ala
            995                 1000                1005

Asn Ser  Gly Val Ile Ser Arg  Gln Phe Phe Ile Asp  Trp Asp Lys
        1010                1015                1020

Tyr Asn  Lys Arg Tyr Ser Thr  Trp Ala Gly Val Ser  Gln Leu Val
        1025                1030                1035

Tyr Tyr  Pro Glu Asn Tyr Ile  Asp Pro Thr Met Arg  Ile Gly Gln
        1040                1045                1050

Thr Lys  Met Met Asp Ala Leu  Leu Gln Ser Val Ser  Gln Ser Gln
        1055                1060                1065

Leu Asn  Ala Asp Thr Val Glu  Asp Ala Phe Met Ser  Tyr Leu Thr
        1070                1075                1080

Ser Phe  Glu Gln Val Ala Asn  Leu Lys Val Ile Ser  Ala Tyr His
        1085                1090                1095

Asp Asn  Ile Asn Asn Asp Gln  Gly Leu Thr Tyr Phe  Ile Gly Leu
        1100                1105                1110

Ser Glu  Thr Asp Ala Gly Glu  Tyr Tyr Trp Arg Ser  Val Asp His
        1115                1120                1125

Ser Lys  Phe Asn Asp Gly Lys  Phe Ala Ala Asn Ala  Trp Ser Glu
        1130                1135                1140

Trp His  Lys Ile Asp Cys Pro  Ile Asn Pro Tyr Lys  Ser Thr Ile
        1145                1150                1155

Arg Pro  Val Ile Tyr Lys Ser  Arg Leu Tyr Leu Leu  Trp Leu Glu
        1160                1165                1170

Gln Lys  Glu Ile Thr Lys Gln  Thr Gly Asn Ser Lys  Asp Gly Tyr
        1175                1180                1185

Gln Thr  Glu Thr Asp Tyr Arg  Tyr Glu Leu Lys Leu  Ala His Ile
        1190                1195                1200

Arg Tyr  Asp Gly Thr Trp Asn  Thr Pro Ile Thr Phe  Asp Val Asn
        1205                1210                1215

Lys Lys  Ile Ser Glu Leu Lys  Leu Glu Lys Asn Arg  Ala Pro Gly
        1220                1225                1230

Leu Tyr  Cys Ala Gly Tyr Gln  Gly Glu Asp Thr Leu  Leu Val Met
```

-continued

```
              1235              1240              1245

Phe Tyr Asn Gln Gln Asp Thr Leu Asp Ser Tyr Lys Asn Ala Ser
    1250              1255              1260

Met Gln Gly Leu Tyr Ile Phe Ala Asp Met Ala Ser Lys Asp Met
    1265              1270              1275

Thr Pro Glu Gln Ser Asn Val Tyr Arg Asp Asn Ser Tyr Gln Gln
    1280              1285              1290

Phe Asp Thr Asn Asn Val Arg Arg Val Asn Asn Arg Tyr Ala Glu
    1295              1300              1305

Asp Tyr Glu Ile Pro Ser Ser Val Ser Ser Arg Lys Asp Tyr Gly
    1310              1315              1320

Trp Gly Asp Tyr Tyr Leu Ser Met Val Tyr Asn Gly Asp Ile Pro
    1325              1330              1335

Thr Ile Asn Tyr Lys Ala Ala Ser Ser Asp Leu Lys Ile Tyr Ile
    1340              1345              1350

Ser Pro Lys Leu Arg Ile Ile His Asn Gly Tyr Glu Gly Gln Lys
    1355              1360              1365

Arg Asn Gln Cys Asn Leu Met Asn Lys Tyr Gly Lys Leu Gly Asp
    1370              1375              1380

Lys Phe Ile Val Tyr Thr Ser Leu Gly Val Asn Pro Asn Asn Ser
    1385              1390              1395

Ser Asn Lys Leu Met Phe Tyr Pro Val Tyr Gln Tyr Ser Gly Asn
    1400              1405              1410

Thr Ser Gly Leu Asn Gln Gly Arg Leu Leu Phe His Arg Asp Thr
    1415              1420              1425

Thr Tyr Pro Ser Lys Val Glu Ala Trp Ile Pro Gly Ala Lys Arg
    1430              1435              1440

Ser Leu Thr Asn Gln Asn Ala Ala Ile Gly Asp Asp Tyr Ala Thr
    1445              1450              1455

Asp Ser Leu Asn Lys Pro Asp Asp Leu Lys Gln Tyr Ile Phe Met
    1460              1465              1470

Thr Asp Ser Lys Gly Thr Ala Thr Asp Val Ser Gly Pro Val Glu
    1475              1480              1485

Ile Asn Thr Ala Ile Ser Pro Ala Lys Val Gln Ile Ile Val Lys
    1490              1495              1500

Ala Gly Gly Lys Glu Gln Thr Phe Thr Ala Asp Lys Asp Val Ser
    1505              1510              1515

Ile Gln Pro Ser Pro Ser Phe Asp Glu Met Asn Tyr Gln Phe Asn
    1520              1525              1530

Ala Leu Glu Ile Asp Gly Ser Gly Leu Asn Phe Ile Asn Asn Ser
    1535              1540              1545

Ala Ser Ile Asp Val Thr Phe Thr Ala Phe Ala Glu Asp Gly Arg
    1550              1555              1560

Lys Leu Gly Tyr Glu Ser Phe Ser Ile Pro Val Thr Leu Lys Val
    1565              1570              1575

Ser Thr Asp Asn Ala Leu Thr Leu His His Asn Glu Asn Gly Ala
    1580              1585              1590

Gln Tyr Met Gln Trp Gln Ser Tyr Arg Thr Arg Leu Asn Thr Leu
    1595              1600              1605

Phe Ala Arg Gln Leu Val Ala Arg Ala Thr Thr Gly Ile Asp Thr
    1610              1615              1620

Ile Leu Ser Met Glu Thr Gln Asn Ile Gln Glu Pro Gln Leu Gly
    1625              1630              1635
```

-continued

```
Lys Gly Phe Tyr Ala Thr Phe Val Ile Pro Pro Tyr Asn Leu Ser
1640                1645                1650

Thr His Gly Asp Glu Arg Trp Phe Lys Leu Tyr Ile Lys His Val
    1655                1660                1665

Val Asp Asn Asn Ser His Ile Ile Tyr Ser Gly Gln Leu Thr Asp
    1670                1675                1680

Thr Asn Ile Asn Ile Thr Leu Phe Ile Pro Leu Asp Asp Val Pro
    1685                1690                1695

Leu Asn Gln Asp Tyr His Ala Lys Val Tyr Met Thr Phe Lys Lys
    1700                1705                1710

Ser Pro Ser Asp Gly Thr Trp Trp Gly Pro His Phe Val Arg Asp
    1715                1720                1725

Asp Lys Gly Ile Val Thr Ile Asn Pro Lys Ser Ile Leu Thr His
    1730                1735                1740

Phe Glu Ser Val Asn Val Leu Asn Asn Ile Ser Ser Glu Pro Met
    1745                1750                1755

Asp Phe Ser Gly Ala Asn Ser Leu Tyr Phe Trp Glu Leu Phe Tyr
    1760                1765                1770

Tyr Thr Pro Met Leu Val Ala Gln Arg Leu Leu His Glu Gln Asn
    1775                1780                1785

Phe Asp Glu Ala Asn Arg Trp Leu Lys Tyr Val Trp Ser Pro Ser
    1790                1795                1800

Gly Tyr Ile Val His Gly Gln Ile Gln Asn Tyr Gln Trp Asn Val
    1805                1810                1815

Arg Pro Leu Leu Glu Asp Thr Ser Trp Asn Ser Asp Pro Leu Asp
    1820                1825                1830

Ser Val Asp Pro Asp Ala Val Ala Gln His Asp Pro Met His Tyr
    1835                1840                1845

Lys Val Ser Thr Phe Met Arg Thr Leu Asp Leu Leu Ile Ala Arg
    1850                1855                1860

Gly Asp His Ala Tyr Arg Gln Leu Glu Arg Asp Thr Leu Asn Glu
    1865                1870                1875

Ala Lys Met Trp Tyr Met Gln Ala Leu His Leu Leu Gly Asp Lys
    1880                1885                1890

Pro Tyr Leu Pro Leu Ser Thr Thr Trp Ser Asp Pro Arg Leu Asp
    1895                1900                1905

Arg Ala Ala Asp Ile Thr Thr Gln Asn Ala His Asp Ser Ala Ile
    1910                1915                1920

Val Ala Leu Arg Gln Asn Ile Pro Thr Pro Ala Pro Leu Ser Leu
    1925                1930                1935

Arg Ser Ala Asn Thr Leu Thr Asp Leu Phe Leu Pro Gln Ile Asn
    1940                1945                1950

Glu Val Met Met Asn Tyr Trp Gln Thr Leu Ala Gln Arg Val Tyr
    1955                1960                1965

Asn Leu Arg His Asn Leu Ser Ile Asp Gly Gln Pro Leu Tyr Leu
    1970                1975                1980

Pro Ile Tyr Ala Thr Pro Ala Asp Pro Lys Ala Leu Leu Ser Ala
    1985                1990                1995

Ala Val Ala Thr Ser Gln Gly Gly Gly Lys Leu Pro Glu Ser Phe
    2000                2005                2010

Met Ser Leu Trp Arg Phe Pro His Met Leu Glu Asn Ala Arg Gly
    2015                2020                2025
```

-continued

| | | | | | | | | | | | |
|---|---|---|---|---|---|---|---|---|---|---|---|
| Met | Val | Ser | Gln | Leu | Thr | Gln | Phe | Gly | Ser | Thr | Leu | Gln | Asn | Ile |
| 2030 | | | | | 2035 | | | | 2040 | | |
| Ile | Glu | Arg | Gln | Asp | Ala | Glu | Ala | Leu | Asn | Ala | Leu | Leu | Gln | Asn |
| 2045 | | | | | 2050 | | | | 2055 | | |
| Gln | Ala | Ala | Glu | Leu | Ile | Leu | Thr | Asn | Leu | Ser | Ile | Gln | Asp | Lys |
| 2060 | | | | | 2065 | | | | 2070 | | |
| Thr | Ile | Glu | Glu | Leu | Asp | Ala | Glu | Lys | Thr | Val | Leu | Glu | Lys | Ser |
| 2075 | | | | | 2080 | | | | 2085 | | |
| Lys | Ala | Gly | Ala | Gln | Ser | Arg | Phe | Asp | Ser | Tyr | Gly | Lys | Leu | Tyr |
| 2090 | | | | | 2095 | | | | 2100 | | |
| Asp | Glu | Asn | Ile | Asn | Ala | Gly | Glu | Asn | Gln | Ala | Met | Thr | Leu | Arg |
| 2105 | | | | | 2110 | | | | 2115 | | |
| Ala | Ser | Ala | Ala | Gly | Leu | Thr | Thr | Ala | Val | Gln | Ala | Ser | Arg | Leu |
| 2120 | | | | | 2125 | | | | 2130 | | |
| Ala | Gly | Ala | Ala | Ala | Asp | Leu | Val | Pro | Asn | Ile | Phe | Gly | Phe | Ala |
| 2135 | | | | | 2140 | | | | 2145 | | |
| Gly | Gly | Gly | Ser | Arg | Trp | Gly | Ala | Ile | Ala | Glu | Ala | Thr | Gly | Tyr |
| 2150 | | | | | 2155 | | | | 2160 | | |
| Val | Met | Glu | Phe | Ser | Ala | Asn | Val | Met | Asn | Thr | Glu | Ala | Asp | Lys |
| 2165 | | | | | 2170 | | | | 2175 | | |
| Ile | Ser | Gln | Ser | Glu | Thr | Tyr | Arg | Arg | Arg | Arg | Gln | Glu | Trp | Glu |
| 2180 | | | | | 2185 | | | | 2190 | | |
| Ile | Gln | Arg | Asn | Asn | Ala | Glu | Ala | Glu | Leu | Lys | Gln | Ile | Asp | Ala |
| 2195 | | | | | 2200 | | | | 2205 | | |
| Gln | Leu | Lys | Ser | Leu | Ala | Val | Arg | Arg | Glu | Ala | Ala | Val | Leu | Gln |
| 2210 | | | | | 2215 | | | | 2220 | | |
| Lys | Thr | Ser | Leu | Lys | Thr | Gln | Gln | Glu | Gln | Thr | Gln | Ser | Gln | Leu |
| 2225 | | | | | 2230 | | | | 2235 | | |
| Ala | Phe | Leu | Gln | Arg | Lys | Phe | Ser | Asn | Gln | Ala | Leu | Tyr | Asn | Trp |
| 2240 | | | | | 2245 | | | | 2250 | | |
| Leu | Arg | Gly | Arg | Leu | Ala | Ala | Ile | Tyr | Phe | Gln | Phe | Tyr | Asp | Leu |
| 2255 | | | | | 2260 | | | | 2265 | | |
| Ala | Val | Ala | Arg | Cys | Leu | Met | Ala | Glu | Gln | Ala | Tyr | Arg | Trp | Glu |
| 2270 | | | | | 2275 | | | | 2280 | | |
| Leu | Asn | Asp | Asp | Ser | Ala | Arg | Phe | Ile | Lys | Pro | Gly | Ala | Trp | Gln |
| 2285 | | | | | 2290 | | | | 2295 | | |
| Gly | Thr | Tyr | Ala | Gly | Leu | Leu | Ala | Gly | Glu | Thr | Leu | Met | Leu | Ser |
| 2300 | | | | | 2305 | | | | 2310 | | |
| Leu | Ala | Gln | Met | Glu | Asp | Ala | His | Leu | Lys | Arg | Asp | Lys | Arg | Ala |
| 2315 | | | | | 2320 | | | | 2325 | | |
| Leu | Glu | Val | Glu | Arg | Thr | Val | Ser | Leu | Ala | Glu | Val | Tyr | Ala | Gly |
| 2330 | | | | | 2335 | | | | 2340 | | |
| Leu | Pro | Lys | Asp | Asn | Gly | Pro | Phe | Ser | Leu | Ala | Gln | Glu | Ile | Asp |
| 2345 | | | | | 2350 | | | | 2355 | | |
| Lys | Leu | Val | Ser | Gln | Gly | Ser | Gly | Ser | Ala | Gly | Ser | Gly | Asn | Asn |
| 2360 | | | | | 2365 | | | | 2370 | | |
| Asn | Leu | Ala | Phe | Gly | Ala | Gly | Thr | Asp | Thr | Lys | Thr | Ser | Leu | Gln |
| 2375 | | | | | 2380 | | | | 2385 | | |
| Ala | Ser | Val | Ser | Phe | Ala | Asp | Leu | Lys | Ile | Arg | Glu | Asp | Tyr | Pro |
| 2390 | | | | | 2395 | | | | 2400 | | |
| Ala | Ser | Leu | Gly | Lys | Ile | Arg | Arg | Ile | Lys | Gln | Ile | Ser | Val | Thr |
| 2405 | | | | | 2410 | | | | 2415 | | |
| Leu | Pro | Ala | Leu | Leu | Gly | Pro | Tyr | Gln | Asp | Val | Gln | Ala | Ile | Leu |

-continued

```
                2420                2425                2430
Ser Tyr Gly Asp Lys Ala Gly Leu Ala Asn Gly Cys Glu Ala Leu
    2435                2440                2445

Ala Val Ser His Gly Met Asn Asp Ser Gly Gln Phe Gln Leu Asp
    2450                2455                2460

Phe Asn Asp Gly Lys Phe Leu Pro Phe Glu Gly Ile Ala Ile Asp
    2465                2470                2475

Gln Gly Thr Leu Thr Leu Ser Phe Pro Asn Ala Ser Met Pro Glu
    2480                2485                2490

Lys Gly Lys Gln Ala Thr Met Leu Lys Thr Leu Asn Asp Ile Ile
    2495                2500                2505

Leu His Ile Arg Tyr Thr Ile Lys
    2510                2515

<210> SEQ ID NO 3
<211> LENGTH: 4431
<212> TYPE: DNA
<213> ORGANISM: Photorhabdus luminescens
<220> FEATURE:
<221> NAME/KEY: CDS
<222> LOCATION: (1)..(4431)

<400> SEQUENCE: 3 atg cag aat tca caa aca ttc agt gtt acc gag ctg tca tta ccc aaa    48
Met Gln Asn Ser Gln Thr Phe Ser Val Thr Glu Leu Ser Leu Pro Lys
1               5                   10                  15 ggc ggc ggc gct att acc ggt atg ggt gaa gca tta aca cca gcc ggg    96
Gly Gly Gly Ala Ile Thr Gly Met Gly Glu Ala Leu Thr Pro Ala Gly
            20                  25                  30 ccg gat ggt atg gcc gcc tta tcc ctg cca tta ccc att tcc gcc ggg   144
Pro Asp Gly Met Ala Ala Leu Ser Leu Pro Leu Pro Ile Ser Ala Gly
        35                  40                  45 cgt ggt tac gca ccc tcg ctc act ctg aat tac aac agt gga acc ggt   192
Arg Gly Tyr Ala Pro Ser Leu Thr Leu Asn Tyr Asn Ser Gly Thr Gly
    50                  55                  60 aac agc cca ttt ggt ctc ggt tgg gac tgc ggc gtc atg gca att cgt   240
Asn Ser Pro Phe Gly Leu Gly Trp Asp Cys Gly Val Met Ala Ile Arg
65                  70                  75                  80 cgt cgc acc agt acc ggc gta ccg aat tac gat gaa acc gat act ttt   288
Arg Arg Thr Ser Thr Gly Val Pro Asn Tyr Asp Glu Thr Asp Thr Phe
                85                  90                  95 ctg ggg ccg gaa ggt gaa gtg ttg gtc gta gca tta aat gag gca ggt   336
Leu Gly Pro Glu Gly Glu Val Leu Val Val Ala Leu Asn Glu Ala Gly
            100                 105                 110 caa gct gat atc cgc agt gaa tcc tca ttg cag ggc atc aat ttg ggt   384
Gln Ala Asp Ile Arg Ser Glu Ser Ser Leu Gln Gly Ile Asn Leu Gly
        115                 120                 125 gcg acc ttc acc gtt acc tgt tat cgc tcc cgc cta gaa agc cac ttt   432
Ala Thr Phe Thr Val Thr Cys Tyr Arg Ser Arg Leu Glu Ser His Phe
    130                 135                 140 aac cgg ttg gaa tac tgg caa ccc caa aca acc ggc gca acc gat ttc   480
Asn Arg Leu Glu Tyr Trp Gln Pro Gln Thr Thr Gly Ala Thr Asp Phe
145                 150                 155                 160 tgg ctg ata tac agc ccc gac gga cag gtc cat tta ctg ggc aaa aat   528
Trp Leu Ile Tyr Ser Pro Asp Gly Gln Val His Leu Leu Gly Lys Asn
                165                 170                 175 cct cag gca cgt atc agc aat cca ctc aat gtt aac caa aca gcg caa   576
Pro Gln Ala Arg Ile Ser Asn Pro Leu Asn Val Asn Gln Thr Ala Gln
            180                 185                 190
```

|   |   |   |   |   |   |   |   |   |   |   |   |   |   |   |   |     |
|---|---|---|---|---|---|---|---|---|---|---|---|---|---|---|---|-----|
| tgg | ctg | ttg | gaa | gcc | tcg | ata | tca | tcc | cac | agc | gaa | cag | att | tat | tat | 624 |
| Trp | Leu | Leu | Glu | Ala | Ser | Ile | Ser | Ser | His | Ser | Glu | Gln | Ile | Tyr | Tyr |     |
|     | 195 |     |     |     |     | 200 |     |     |     |     | 205 |     |     |     |     |     |

|   |   |   |   |   |   |   |   |   |   |   |   |   |   |   |   |     |
|---|---|---|---|---|---|---|---|---|---|---|---|---|---|---|---|-----|
| caa | tat | cgc | gct | gaa | gat | gaa | gca | ggt | tgt | gaa | acc | gac | gag | cta | gca | 672 |
| Gln | Tyr | Arg | Ala | Glu | Asp | Glu | Ala | Gly | Cys | Glu | Thr | Asp | Glu | Leu | Ala |     |
| 210 |     |     |     |     | 215 |     |     |     |     | 220 |     |     |     |     |     |     |

|   |   |   |   |   |   |   |   |   |   |   |   |   |   |   |   |     |
|---|---|---|---|---|---|---|---|---|---|---|---|---|---|---|---|-----|
| gcc | cac | ccc | agc | gca | acc | gtt | cag | cgc | tac | ctg | caa | aca | gta | cat | tac | 720 |
| Ala | His | Pro | Ser | Ala | Thr | Val | Gln | Arg | Tyr | Leu | Gln | Thr | Val | His | Tyr |     |
| 225 |     |     |     |     | 230 |     |     |     |     | 235 |     |     |     |     | 240 |     |

|   |   |   |   |   |   |   |   |   |   |   |   |   |   |   |   |     |
|---|---|---|---|---|---|---|---|---|---|---|---|---|---|---|---|-----|
| ggg | aac | ctg | acc | gcc | agc | gac | gtt | ttt | cct | aca | cta | aac | gga | gat | gac | 768 |
| Gly | Asn | Leu | Thr | Ala | Ser | Asp | Val | Phe | Pro | Thr | Leu | Asn | Gly | Asp | Asp |     |
|     |     |     |     | 245 |     |     |     |     | 250 |     |     |     |     | 255 |     |     |

|   |   |   |   |   |   |   |   |   |   |   |   |   |   |   |   |     |
|---|---|---|---|---|---|---|---|---|---|---|---|---|---|---|---|-----|
| cca | ctt | aaa | tct | ggc | tgg | atg | ttc | tgt | tta | gta | ttt | gac | tac | ggt | gag | 816 |
| Pro | Leu | Lys | Ser | Gly | Trp | Met | Phe | Cys | Leu | Val | Phe | Asp | Tyr | Gly | Glu |     |
|     |     |     | 260 |     |     |     |     | 265 |     |     |     |     | 270 |     |     |     |

|   |   |   |   |   |   |   |   |   |   |   |   |   |   |   |   |     |
|---|---|---|---|---|---|---|---|---|---|---|---|---|---|---|---|-----|
| cgc | aaa | aac | agc | tta | tct | gaa | atg | ccg | ctg | ttt | aaa | gcc | aca | ggc | aat | 864 |
| Arg | Lys | Asn | Ser | Leu | Ser | Glu | Met | Pro | Leu | Phe | Lys | Ala | Thr | Gly | Asn |     |
|     |     | 275 |     |     |     |     | 280 |     |     |     |     | 285 |     |     |     |     |

|   |   |   |   |   |   |   |   |   |   |   |   |   |   |   |   |     |
|---|---|---|---|---|---|---|---|---|---|---|---|---|---|---|---|-----|
| tgg | ctt | tgc | cga | aaa | gac | cgt | ttt | tcc | cgt | tat | gag | tac | ggt | ttt | gaa | 912 |
| Trp | Leu | Cys | Arg | Lys | Asp | Arg | Phe | Ser | Arg | Tyr | Glu | Tyr | Gly | Phe | Glu |     |
| 290 |     |     |     |     | 295 |     |     |     |     | 300 |     |     |     |     |     |     |

|   |   |   |   |   |   |   |   |   |   |   |   |   |   |   |   |     |
|---|---|---|---|---|---|---|---|---|---|---|---|---|---|---|---|-----|
| ttg | cgt | act | cgc | cgc | tta | tgc | cgc | caa | ata | ctg | atg | ttt | cac | cgt | cta | 960 |
| Leu | Arg | Thr | Arg | Arg | Leu | Cys | Arg | Gln | Ile | Leu | Met | Phe | His | Arg | Leu |     |
| 305 |     |     |     |     | 310 |     |     |     |     | 315 |     |     |     |     | 320 |     |

|   |   |   |   |   |   |   |   |   |   |   |   |   |   |   |   |      |
|---|---|---|---|---|---|---|---|---|---|---|---|---|---|---|---|------|
| caa | acc | cta | tct | ggt | cag | gca | aag | ggg | gat | gat | gaa | cct | gcg | cta | gtg | 1008 |
| Gln | Thr | Leu | Ser | Gly | Gln | Ala | Lys | Gly | Asp | Asp | Glu | Pro | Ala | Leu | Val |      |
|     |     |     |     | 325 |     |     |     |     | 330 |     |     |     |     | 335 |     |      |

|   |   |   |   |   |   |   |   |   |   |   |   |   |   |   |   |      |
|---|---|---|---|---|---|---|---|---|---|---|---|---|---|---|---|------|
| tcg | cgt | ctg | ata | ctg | gat | tat | gac | gaa | aac | gcg | atg | gtc | agt | acg | ctc | 1056 |
| Ser | Arg | Leu | Ile | Leu | Asp | Tyr | Asp | Glu | Asn | Ala | Met | Val | Ser | Thr | Leu |      |
|     |     |     | 340 |     |     |     |     | 345 |     |     |     |     | 350 |     |     |      |

|   |   |   |   |   |   |   |   |   |   |   |   |   |   |   |   |      |
|---|---|---|---|---|---|---|---|---|---|---|---|---|---|---|---|------|
| gtt | tct | gtc | cgc | cgg | gta | ggc | cat | gag | gac | aac | aac | acg | gtt | acc | gcg | 1104 |
| Val | Ser | Val | Arg | Arg | Val | Gly | His | Glu | Asp | Asn | Asn | Thr | Val | Thr | Ala |      |
|     |     | 355 |     |     |     |     | 360 |     |     |     |     | 365 |     |     |     |      |

|   |   |   |   |   |   |   |   |   |   |   |   |   |   |   |   |      |
|---|---|---|---|---|---|---|---|---|---|---|---|---|---|---|---|------|
| ctg | cca | cca | ctg | gaa | ctg | gcc | tat | cag | cct | ttt | gag | cca | gaa | caa | acc | 1152 |
| Leu | Pro | Pro | Leu | Glu | Leu | Ala | Tyr | Gln | Pro | Phe | Glu | Pro | Glu | Gln | Thr |      |
| 370 |     |     |     |     | 375 |     |     |     |     | 380 |     |     |     |     |     |      |

|   |   |   |   |   |   |   |   |   |   |   |   |   |   |   |   |      |
|---|---|---|---|---|---|---|---|---|---|---|---|---|---|---|---|------|
| gca | ctc | tgg | caa | tca | atg | gat | gta | ctg | gca | aat | ttc | aac | acc | att | cag | 1200 |
| Ala | Leu | Trp | Gln | Ser | Met | Asp | Val | Leu | Ala | Asn | Phe | Asn | Thr | Ile | Gln |      |
| 385 |     |     |     |     | 390 |     |     |     |     | 395 |     |     |     |     | 400 |      |

|   |   |   |   |   |   |   |   |   |   |   |   |   |   |   |   |      |
|---|---|---|---|---|---|---|---|---|---|---|---|---|---|---|---|------|
| cgc | tgg | caa | ctg | ctt | gac | ctg | aaa | gga | gaa | ggc | gtg | ccc | ggc | att | ctc | 1248 |
| Arg | Trp | Gln | Leu | Leu | Asp | Leu | Lys | Gly | Glu | Gly | Val | Pro | Gly | Ile | Leu |      |
|     |     |     |     | 405 |     |     |     |     | 410 |     |     |     |     | 415 |     |      |

|   |   |   |   |   |   |   |   |   |   |   |   |   |   |   |   |      |
|---|---|---|---|---|---|---|---|---|---|---|---|---|---|---|---|------|
| tat | cag | gat | aga | aat | ggc | tgg | tgg | tat | cga | tct | gcc | caa | cgt | cag | gcc | 1296 |
| Tyr | Gln | Asp | Arg | Asn | Gly | Trp | Trp | Tyr | Arg | Ser | Ala | Gln | Arg | Gln | Ala |      |
|     |     |     | 420 |     |     |     |     | 425 |     |     |     |     | 430 |     |     |      |

|   |   |   |   |   |   |   |   |   |   |   |   |   |   |   |   |      |
|---|---|---|---|---|---|---|---|---|---|---|---|---|---|---|---|------|
| ggg | gaa | gag | atg | aat | gcg | gtc | acc | tgg | ggg | aaa | atg | caa | ctc | ctt | ccc | 1344 |
| Gly | Glu | Glu | Met | Asn | Ala | Val | Thr | Trp | Gly | Lys | Met | Gln | Leu | Leu | Pro |      |
|     |     | 435 |     |     |     |     | 440 |     |     |     |     | 445 |     |     |     |      |

|   |   |   |   |   |   |   |   |   |   |   |   |   |   |   |   |      |
|---|---|---|---|---|---|---|---|---|---|---|---|---|---|---|---|------|
| atc | aca | cca | gct | gtg | cag | gat | aac | gcc | tca | ctg | atg | gat | att | aac | ggt | 1392 |
| Ile | Thr | Pro | Ala | Val | Gln | Asp | Asn | Ala | Ser | Leu | Met | Asp | Ile | Asn | Gly |      |
|     | 450 |     |     |     |     | 455 |     |     |     |     | 460 |     |     |     |     |      |

|   |   |   |   |   |   |   |   |   |   |   |   |   |   |   |   |      |
|---|---|---|---|---|---|---|---|---|---|---|---|---|---|---|---|------|
| gac | ggg | caa | ctg | gac | tgg | gtg | att | acc | ggg | ccg | ggc | cta | agg | ggc | tat | 1440 |
| Asp | Gly | Gln | Leu | Asp | Trp | Val | Ile | Thr | Gly | Pro | Gly | Leu | Arg | Gly | Tyr |      |
| 465 |     |     |     |     | 470 |     |     |     |     | 475 |     |     |     |     | 480 |      |

|   |   |   |   |   |   |   |   |   |   |   |   |   |   |   |   |      |
|---|---|---|---|---|---|---|---|---|---|---|---|---|---|---|---|------|
| cac | agc | caa | cac | ccg | gat | ggc | agt | tgg | acg | cgt | ttt | acg | cca | tta | cat | 1488 |
| His | Ser | Gln | His | Pro | Asp | Gly | Ser | Trp | Thr | Arg | Phe | Thr | Pro | Leu | His |      |
|     |     |     |     | 485 |     |     |     |     | 490 |     |     |     |     | 495 |     |      |

|   |   |   |   |   |   |   |   |   |   |   |   |   |   |   |   |      |
|---|---|---|---|---|---|---|---|---|---|---|---|---|---|---|---|------|
| gcc | ctg | ccg | ata | gaa | tat | tct | cat | cct | cgc | gct | caa | ctt | gcc | gat | tta | 1536 |
| Ala | Leu | Pro | Ile | Glu | Tyr | Ser | His | Pro | Arg | Ala | Gln | Leu | Ala | Asp | Leu |      |
|     |     |     | 500 |     |     |     |     | 505 |     |     |     |     | 510 |     |     |      |

```
atg gga gcc ggg ctg tcc gat tta gtg cta att ggt ccc aaa agt gtg      1584
Met Gly Ala Gly Leu Ser Asp Leu Val Leu Ile Gly Pro Lys Ser Val
        515                 520                 525 cgc tta tat gtc aat aac cgt gat ggt ttt acc gaa ggg cgg gat gtg      1632
Arg Leu Tyr Val Asn Asn Arg Asp Gly Phe Thr Glu Gly Arg Asp Val
530                 535                 540 gtg caa tcc ggt gat atc acc ctg ccg cta ccg ggc gcc gat gcc cgt      1680
Val Gln Ser Gly Asp Ile Thr Leu Pro Leu Pro Gly Ala Asp Ala Arg
545                 550                 555                 560 aag tta gtg gca ttt agt gac gta ctg ggt tca ggc caa gca cat ctg      1728
Lys Leu Val Ala Phe Ser Asp Val Leu Gly Ser Gly Gln Ala His Leu
                565                 570                 575 gtt gaa gtt agt gca act caa gtc acc tgc tgg ccg aat ctg ggg cat      1776
Val Glu Val Ser Ala Thr Gln Val Thr Cys Trp Pro Asn Leu Gly His
            580                 585                 590 ggc cgt ttt ggt cag cca atc gta ttg ccg gga ttc agc caa tct gcc      1824
Gly Arg Phe Gly Gln Pro Ile Val Leu Pro Gly Phe Ser Gln Ser Ala
        595                 600                 605 gcc agt ttt aat cct gat cga gtt cat ctg gcc gat ttg gat ggg agc      1872
Ala Ser Phe Asn Pro Asp Arg Val His Leu Ala Asp Leu Asp Gly Ser
610                 615                 620 ggc cct gcc gat ttg att tat gtt cat gct gac cgt ctg gat att ttc      1920
Gly Pro Ala Asp Leu Ile Tyr Val His Ala Asp Arg Leu Asp Ile Phe
625                 630                 635                 640 agc aat gaa agt ggc aac ggt ttt gca aaa cca ttc aca ctc tct ttt      1968
Ser Asn Glu Ser Gly Asn Gly Phe Ala Lys Pro Phe Thr Leu Ser Phe
                645                 650                 655 cct gac ggc ctg cgt ttt gat gat acc tgc cag ttg caa gta gcc gat      2016
Pro Asp Gly Leu Arg Phe Asp Asp Thr Cys Gln Leu Gln Val Ala Asp
            660                 665                 670 gta caa ggg tta ggc gtt gtc agc ctg atc cta agc gta ccg cat atg      2064
Val Gln Gly Leu Gly Val Val Ser Leu Ile Leu Ser Val Pro His Met
        675                 680                 685 gcg cca cat cat tgg cgc tgc gat ctg acc aac gcg aaa ccg tgg tta      2112
Ala Pro His His Trp Arg Cys Asp Leu Thr Asn Ala Lys Pro Trp Leu
690                 695                 700 ctc agt gaa acg aac aac aat atg ggg gcc aat cac acc ttg cat tac      2160
Leu Ser Glu Thr Asn Asn Asn Met Gly Ala Asn His Thr Leu His Tyr
705                 710                 715                 720 cgt agc tct gtc cag ttc tgg ctg gat gaa aaa gct gcg gca ttg gct      2208
Arg Ser Ser Val Gln Phe Trp Leu Asp Glu Lys Ala Ala Ala Leu Ala
                725                 730                 735 acc gga caa aca ccg gtc tgt tac ctg ccc ttc ccg gtc cat acc ctt      2256
Thr Gly Gln Thr Pro Val Cys Tyr Leu Pro Phe Pro Val His Thr Leu
            740                 745                 750 tgg caa aca gaa acc gag gat gaa atc agc ggc aat aag tta gtg acc      2304
Trp Gln Thr Glu Thr Glu Asp Glu Ile Ser Gly Asn Lys Leu Val Thr
        755                 760                 765 acg tta cgt tat gct cac ggc gct tgg gat gga cgt gaa cgg gaa ttt      2352
Thr Leu Arg Tyr Ala His Gly Ala Trp Asp Gly Arg Glu Arg Glu Phe
770                 775                 780 cgt ggc ttt ggt tat gtt gag cag aca gac agc cat caa ctc gct caa      2400
Arg Gly Phe Gly Tyr Val Glu Gln Thr Asp Ser His Gln Leu Ala Gln
785                 790                 795                 800 ggc aat gcg ccg gaa cgt aca cca ccg gca ctc acc aaa agc tgg tat      2448
Gly Asn Ala Pro Glu Arg Thr Pro Pro Ala Leu Thr Lys Ser Trp Tyr
                805                 810                 815 gcc acc gga tta cct gcg gta gat aat gcg tta tcc gcc ggg tat tgg      2496
Ala Thr Gly Leu Pro Ala Val Asp Asn Ala Leu Ser Ala Gly Tyr Trp
```

-continued

|                                                                                                                     |      |
|---------------------------------------------------------------------------------------------------------------------|------|
| 820                           825                           830                                                     |      |
| cgt ggc gat aag caa gct ttc gcc ggt ttt acg cca cgt ttt act ctc<br>Arg Gly Asp Lys Gln Ala Phe Ala Gly Phe Thr Pro Arg Phe Thr Leu<br>835             840             845 | 2544 |
| tgg aaa gag ggc aaa gat gtt cca ctg aca ccg gaa gat gac cat aat<br>Trp Lys Glu Gly Lys Asp Val Pro Leu Thr Pro Glu Asp Asp His Asn<br>850             855             860 | 2592 |
| cta tac tgg tta aac cgg gcg cta aaa ggt cag cca ctg cgt agt gaa<br>Leu Tyr Trp Leu Asn Arg Ala Leu Lys Gly Gln Pro Leu Arg Ser Glu<br>865             870             875             880 | 2640 |
| ctc tac ggg ctg gat ggc agc gca cag caa cag atc ccc tat aca gtg<br>Leu Tyr Gly Leu Asp Gly Ser Ala Gln Gln Gln Ile Pro Tyr Thr Val<br>885             890             895 | 2688 |
| act gaa tcc cgt cca cag gtg cgc caa tta caa gat ggc gcc acc gtt<br>Thr Glu Ser Arg Pro Gln Val Arg Gln Leu Gln Asp Gly Ala Thr Val<br>900             905             910 | 2736 |
| tcc ccg gtg ctc tgg gcc tca gtc gtg gaa agc cgt agt tat cac tac<br>Ser Pro Val Leu Trp Ala Ser Val Val Glu Ser Arg Ser Tyr His Tyr<br>915             920             925 | 2784 |
| gaa cgt att atc agt gat ccc cag tgc aat cag gat atc acg ttg tcc<br>Glu Arg Ile Ile Ser Asp Pro Gln Cys Asn Gln Asp Ile Thr Leu Ser<br>930             935             940 | 2832 |
| agt gac cta ttc ggg caa cca ctg aaa cag gtt tcc gta caa tat ccc<br>Ser Asp Leu Phe Gly Gln Pro Leu Lys Gln Val Ser Val Gln Tyr Pro<br>945             950             955             960 | 2880 |
| cgc cgc aac aaa cca aca acc aat ccg tat ccc gat acc cta ccg gat<br>Arg Arg Asn Lys Pro Thr Thr Asn Pro Tyr Pro Asp Thr Leu Pro Asp<br>965             970             975 | 2928 |
| acg ctg ttt gcc agc agt tat gac gat caa caa cag cta ttg cga tta<br>Thr Leu Phe Ala Ser Ser Tyr Asp Asp Gln Gln Gln Leu Leu Arg Leu<br>980             985             990 | 2976 |
| acc tgc cga caa tcc agt tgg cac cat ctt att ggt aat gag cta aga<br>Thr Cys Arg Gln Ser Ser Trp His His Leu Ile Gly Asn Glu Leu Arg<br>995             1000            1005 | 3024 |
| gtg ttg gga tta ccg gat ggc aca cgc agt gat gcc ttt act tac<br>Val Leu Gly Leu Pro Asp Gly Thr Arg Ser Asp Ala Phe Thr Tyr<br>1010            1015            1020 | 3069 |
| gat gcc aaa cag gta cct gtc gat ggc tta aat ctg gaa acc ctg<br>Asp Ala Lys Gln Val Pro Val Asp Gly Leu Asn Leu Glu Thr Leu<br>1025            1030            1035 | 3114 |
| tgt gct gaa aat agc ctg att gcc gat gat aaa cct cgc gaa tac<br>Cys Ala Glu Asn Ser Leu Ile Ala Asp Asp Lys Pro Arg Glu Tyr<br>1040            1045            1050 | 3159 |
| ctc aat cag caa cga acg ttc tat acc gac ggg aaa aac caa aca<br>Leu Asn Gln Gln Arg Thr Phe Tyr Thr Asp Gly Lys Asn Gln Thr<br>1055            1060            1065 | 3204 |
| ccg ctg aaa aca ccg aca cga caa gcg tta atc gcc ttt acc gaa<br>Pro Leu Lys Thr Pro Thr Arg Gln Ala Leu Ile Ala Phe Thr Glu<br>1070            1075            1080 | 3249 |
| acg gcg gta tta acg gaa tct ctg tta tcc gcg ttt gat ggc ggt<br>Thr Ala Val Leu Thr Glu Ser Leu Leu Ser Ala Phe Asp Gly Gly<br>1085            1090            1095 | 3294 |
| att acg cca gac gaa tta ccg gga ata ctg aca cag gcc gga tac<br>Ile Thr Pro Asp Glu Leu Pro Gly Ile Leu Thr Gln Ala Gly Tyr<br>1100            1105            1110 | 3339 |
| caa caa gag cct tat ctg ttt cca cgc acc ggc gaa aac aaa gtt<br>Gln Gln Glu Pro Tyr Leu Phe Pro Arg Thr Gly Glu Asn Lys Val<br>1115            1120            1125 | 3384 |
| tgg gta gcg cgt caa ggc tat acc gat tac ggg acg gaa gca caa<br>Trp Val Ala Arg Gln Gly Tyr Thr Asp Tyr Gly Thr Glu Ala Gln | 3429 |

|   |   |   |   |   |   |   |   |   |   |   |   |   |
|---|---|---|---|---|---|---|---|---|---|---|---|---|
| Trp | Val | Ala | Arg | Gln | Gly | Tyr | Thr | Asp | Tyr | Gly | Thr | Glu Ala Gln |
| 1130 | | | | | 1135 | | | | 1140 | | | |

| ttt | tgg | cgt | cct | gtc | gca | caa | cgt | aac | agc | ctg | tta | acc ggg aaa | 3474 |
|---|---|---|---|---|---|---|---|---|---|---|---|---|---|
| Phe | Trp | Arg | Pro | Val | Ala | Gln | Arg | Asn | Ser | Leu | Leu | Thr Gly Lys | |
| 1145 | | | | 1150 | | | | | 1155 | | | | |

| atg | acg | tta | aaa | tgg | gat | act | cac | tat | tgt | gtc | atc | acc caa acc | 3519 |
|---|---|---|---|---|---|---|---|---|---|---|---|---|---|
| Met | Thr | Leu | Lys | Trp | Asp | Thr | His | Tyr | Cys | Val | Ile | Thr Gln Thr | |
| 1160 | | | | | 1165 | | | | 1170 | | | | |

| caa | gat | gct | gcc | ggc | ctc | acc | gtc | tca | gcc | aat | tat | gac tgg cgt | 3564 |
|---|---|---|---|---|---|---|---|---|---|---|---|---|---|
| Gln | Asp | Ala | Ala | Gly | Leu | Thr | Val | Ser | Ala | Asn | Tyr | Asp Trp Arg | |
| 1175 | | | | 1180 | | | | | 1185 | | | | |

| ttt | ctc | aca | cca | acg | caa | ctg | act | gac | atc | aac | gat | aat gtg cat | 3609 |
|---|---|---|---|---|---|---|---|---|---|---|---|---|---|
| Phe | Leu | Thr | Pro | Thr | Gln | Leu | Thr | Asp | Ile | Asn | Asp | Asn Val His | |
| 1190 | | | | | 1195 | | | | 1200 | | | | |

| ctc | atc | acc | ttg | gat | gct | ctg | gga | cgc | cct | gtc | acg | caa cgt ttc | 3654 |
|---|---|---|---|---|---|---|---|---|---|---|---|---|---|
| Leu | Ile | Thr | Leu | Asp | Ala | Leu | Gly | Arg | Pro | Val | Thr | Gln Arg Phe | |
| 1205 | | | | 1210 | | | | | 1215 | | | | |

| tgg | ggg | atc | gaa | agc | ggt | gtg | gca | aca | ggt | tac | tct | tca tca gaa | 3699 |
|---|---|---|---|---|---|---|---|---|---|---|---|---|---|
| Trp | Gly | Ile | Glu | Ser | Gly | Val | Ala | Thr | Gly | Tyr | Ser | Ser Ser Glu | |
| 1220 | | | | | 1225 | | | | 1230 | | | | |

| gaa | aaa | cca | ttc | tct | cca | cca | aac | gat | atc | gat | acc | gct att aat | 3744 |
|---|---|---|---|---|---|---|---|---|---|---|---|---|---|
| Glu | Lys | Pro | Phe | Ser | Pro | Pro | Asn | Asp | Ile | Asp | Thr | Ala Ile Asn | |
| 1235 | | | | 1240 | | | | | 1245 | | | | |

| cta | acc | gga | cca | ctc | cct | gtc | gca | cag | tgt | ctg | gtc | tat gca ccg | 3789 |
|---|---|---|---|---|---|---|---|---|---|---|---|---|---|
| Leu | Thr | Gly | Pro | Leu | Pro | Val | Ala | Gln | Cys | Leu | Val | Tyr Ala Pro | |
| 1250 | | | | | 1255 | | | | 1260 | | | | |

| gac | agt | tgg | atg | cca | cta | ttc | agt | caa | gaa | acc | ttc | aac aca tta | 3834 |
|---|---|---|---|---|---|---|---|---|---|---|---|---|---|
| Asp | Ser | Trp | Met | Pro | Leu | Phe | Ser | Gln | Glu | Thr | Phe | Asn Thr Leu | |
| 1265 | | | | 1270 | | | | | 1275 | | | | |

| acg | cag | gaa | gag | cag | gag | acg | ctg | cgt | gat | tca | cgt | att atc acg | 3879 |
|---|---|---|---|---|---|---|---|---|---|---|---|---|---|
| Thr | Gln | Glu | Glu | Gln | Glu | Thr | Leu | Arg | Asp | Ser | Arg | Ile Ile Thr | |
| 1280 | | | | | 1285 | | | | 1290 | | | | |

| gaa | gat | tgg | cgt | att | tgc | gca | ctg | act | cgc | cgc | cgt | tgg cta caa | 3924 |
|---|---|---|---|---|---|---|---|---|---|---|---|---|---|
| Glu | Asp | Trp | Arg | Ile | Cys | Ala | Leu | Thr | Arg | Arg | Arg | Trp Leu Gln | |
| 1295 | | | | 1300 | | | | | 1305 | | | | |

| agt | caa | aag | atc | agt | aca | cca | tta | gtt | aaa | ctg | tta | acc aac agc | 3969 |
|---|---|---|---|---|---|---|---|---|---|---|---|---|---|
| Ser | Gln | Lys | Ile | Ser | Thr | Pro | Leu | Val | Lys | Leu | Leu | Thr Asn Ser | |
| 1310 | | | | | 1315 | | | | 1320 | | | | |

| att | ggt | tta | cct | ccc | cat | aac | ctt | acg | ctg | acc | aca | gac cgt tat | 4014 |
|---|---|---|---|---|---|---|---|---|---|---|---|---|---|
| Ile | Gly | Leu | Pro | Pro | His | Asn | Leu | Thr | Leu | Thr | Thr | Asp Arg Tyr | |
| 1325 | | | | 1330 | | | | | 1335 | | | | |

| gac | cgc | gac | tct | gag | cag | caa | att | cgc | caa | caa | gtc | gca ttt agt | 4059 |
|---|---|---|---|---|---|---|---|---|---|---|---|---|---|
| Asp | Arg | Asp | Ser | Glu | Gln | Gln | Ile | Arg | Gln | Gln | Val | Ala Phe Ser | |
| 1340 | | | | | 1345 | | | | 1350 | | | | |

| gat | ggt | ttt | ggc | cgt | ctg | cta | caa | gcg | tct | gta | cga | cat gag gca | 4104 |
|---|---|---|---|---|---|---|---|---|---|---|---|---|---|
| Asp | Gly | Phe | Gly | Arg | Leu | Leu | Gln | Ala | Ser | Val | Arg | His Glu Ala | |
| 1355 | | | | 1360 | | | | | 1365 | | | | |

| ggc | gaa | gcc | tgg | caa | cgt | aac | caa | gac | ggt | tct | ctg | gtg aca aaa | 4149 |
|---|---|---|---|---|---|---|---|---|---|---|---|---|---|
| Gly | Glu | Ala | Trp | Gln | Arg | Asn | Gln | Asp | Gly | Ser | Leu | Val Thr Lys | |
| 1370 | | | | | 1375 | | | | 1380 | | | | |

| gtg | gag | aat | acc | aaa | acg | cgt | tgg | gcg | gtc | acg | gga | cgc acc gaa | 4194 |
|---|---|---|---|---|---|---|---|---|---|---|---|---|---|
| Val | Glu | Asn | Thr | Lys | Thr | Arg | Trp | Ala | Val | Thr | Gly | Arg Thr Glu | |
| 1385 | | | | 1390 | | | | | 1395 | | | | |

| tat | gat | aat | aaa | ggg | caa | acg | ata | cgc | act | tat | cag | ccc tat ttc | 4239 |
|---|---|---|---|---|---|---|---|---|---|---|---|---|---|
| Tyr | Asp | Asn | Lys | Gly | Gln | Thr | Ile | Arg | Thr | Tyr | Gln | Pro Tyr Phe | |
| 1400 | | | | | 1405 | | | | 1410 | | | | |

| ctc | aac | gac | tgg | cga | tat | gtc | agt | gat | gac | agc | gcc | aga aaa gaa | 4284 |
|---|---|---|---|---|---|---|---|---|---|---|---|---|---|
| Leu | Asn | Asp | Trp | Arg | Tyr | Val | Ser | Asp | Asp | Ser | Ala | Arg Lys Glu | |
| 1415 | | | | 1420 | | | | | 1425 | | | | |

```
gcc tat gcg gat act cat att tat gat cca att ggg cga gaa atc    4329
Ala Tyr Ala Asp Thr His Ile Tyr Asp Pro Ile Gly Arg Glu Ile
    1430            1435            1440 cgg gtt att act gca aaa ggc tgg ctg cgc caa agc caa tat ttc    4374
Arg Val Ile Thr Ala Lys Gly Trp Leu Arg Gln Ser Gln Tyr Phe
1445            1450            1455 ccg tgg ttt acc gtg agt gag gat gag aat gat acg gcc gct gat    4419
Pro Trp Phe Thr Val Ser Glu Asp Glu Asn Asp Thr Ala Ala Asp
    1460            1465            1470 gcg ctg gtg taa                                                 4431
Ala Leu Val
    1475
```

<210> SEQ ID NO 4
<211> LENGTH: 1476
<212> TYPE: PRT
<213> ORGANISM: Photorhabdus luminescens

<400> SEQUENCE: 4

```
Met Gln Asn Ser Gln Thr Phe Ser Val Thr Glu Leu Ser Leu Pro Lys
1               5                   10                  15

Gly Gly Gly Ala Ile Thr Gly Met Gly Glu Ala Leu Thr Pro Ala Gly
            20                  25                  30

Pro Asp Gly Met Ala Ala Leu Ser Leu Pro Leu Pro Ile Ser Ala Gly
        35                  40                  45

Arg Gly Tyr Ala Pro Ser Leu Thr Leu Asn Tyr Asn Ser Gly Thr Gly
    50                  55                  60

Asn Ser Pro Phe Gly Leu Gly Trp Asp Cys Gly Val Met Ala Ile Arg
65                  70                  75                  80

Arg Arg Thr Ser Thr Gly Val Pro Asn Tyr Asp Glu Thr Asp Thr Phe
                85                  90                  95

Leu Gly Pro Glu Gly Glu Val Leu Val Ala Leu Asn Glu Ala Gly
            100                 105                 110

Gln Ala Asp Ile Arg Ser Glu Ser Ser Leu Gln Gly Ile Asn Leu Gly
        115                 120                 125

Ala Thr Phe Thr Val Thr Cys Tyr Arg Ser Arg Leu Glu Ser His Phe
    130                 135                 140

Asn Arg Leu Glu Tyr Trp Gln Pro Gln Thr Thr Gly Ala Thr Asp Phe
145                 150                 155                 160

Trp Leu Ile Tyr Ser Pro Asp Gly Gln Val His Leu Leu Gly Lys Asn
                165                 170                 175

Pro Gln Ala Arg Ile Ser Asn Pro Leu Asn Val Asn Gln Thr Ala Gln
            180                 185                 190

Trp Leu Leu Glu Ala Ser Ile Ser Ser His Ser Glu Gln Ile Tyr Tyr
        195                 200                 205

Gln Tyr Arg Ala Glu Asp Glu Ala Gly Cys Glu Thr Asp Glu Leu Ala
    210                 215                 220

Ala His Pro Ser Ala Thr Val Gln Arg Tyr Leu Gln Thr Val His Tyr
225                 230                 235                 240

Gly Asn Leu Thr Ala Ser Asp Val Phe Pro Thr Leu Asn Gly Asp Asp
                245                 250                 255

Pro Leu Lys Ser Gly Trp Met Phe Cys Leu Val Phe Asp Tyr Gly Glu
            260                 265                 270

Arg Lys Asn Ser Leu Ser Glu Met Pro Leu Phe Lys Ala Thr Gly Asn
        275                 280                 285

Trp Leu Cys Arg Lys Asp Arg Phe Ser Arg Tyr Glu Tyr Gly Phe Glu
```

-continued

```
            290                 295                 300
Leu Arg Thr Arg Arg Leu Cys Arg Gln Ile Leu Met Phe His Arg Leu
305                 310                 315                 320

Gln Thr Leu Ser Gly Gln Ala Lys Gly Asp Asp Glu Pro Ala Leu Val
                325                 330                 335

Ser Arg Leu Ile Leu Asp Tyr Asp Glu Asn Ala Met Val Ser Thr Leu
                340                 345                 350

Val Ser Val Arg Arg Val Gly His Glu Asp Asn Asn Thr Val Thr Ala
                355                 360                 365

Leu Pro Pro Leu Glu Leu Ala Tyr Gln Pro Phe Glu Pro Glu Gln Thr
370                 375                 380

Ala Leu Trp Gln Ser Met Asp Val Leu Ala Asn Phe Asn Thr Ile Gln
385                 390                 395                 400

Arg Trp Gln Leu Leu Asp Leu Lys Gly Glu Gly Val Pro Gly Ile Leu
                405                 410                 415

Tyr Gln Asp Arg Asn Gly Trp Trp Tyr Arg Ser Ala Gln Arg Gln Ala
                420                 425                 430

Gly Glu Glu Met Asn Ala Val Thr Trp Gly Lys Met Gln Leu Leu Pro
                435                 440                 445

Ile Thr Pro Ala Val Gln Asp Asn Ala Ser Leu Met Asp Ile Asn Gly
            450                 455                 460

Asp Gly Gln Leu Asp Trp Val Ile Thr Gly Pro Gly Leu Arg Gly Tyr
465                 470                 475                 480

His Ser Gln His Pro Asp Gly Ser Trp Thr Arg Phe Thr Pro Leu His
                485                 490                 495

Ala Leu Pro Ile Glu Tyr Ser His Pro Arg Ala Gln Leu Ala Asp Leu
                500                 505                 510

Met Gly Ala Gly Leu Ser Asp Leu Val Leu Ile Gly Pro Lys Ser Val
            515                 520                 525

Arg Leu Tyr Val Asn Asn Arg Asp Gly Phe Thr Glu Gly Arg Asp Val
                530                 535                 540

Val Gln Ser Gly Asp Ile Thr Leu Pro Leu Pro Gly Ala Asp Ala Arg
545                 550                 555                 560

Lys Leu Val Ala Phe Ser Asp Val Leu Gly Ser Gly Gln Ala His Leu
                565                 570                 575

Val Glu Val Ser Ala Thr Gln Val Thr Cys Trp Pro Asn Leu Gly His
                580                 585                 590

Gly Arg Phe Gly Gln Pro Ile Val Leu Pro Gly Phe Ser Gln Ser Ala
            595                 600                 605

Ala Ser Phe Asn Pro Asp Arg Val His Leu Ala Asp Leu Asp Gly Ser
            610                 615                 620

Gly Pro Ala Asp Leu Ile Tyr Val His Ala Asp Arg Leu Asp Ile Phe
625                 630                 635                 640

Ser Asn Glu Ser Gly Asn Gly Phe Ala Lys Pro Phe Thr Leu Ser Phe
                645                 650                 655

Pro Asp Gly Leu Arg Phe Asp Asp Thr Cys Gln Leu Gln Val Ala Asp
                660                 665                 670

Val Gln Gly Leu Gly Val Val Ser Leu Ile Leu Ser Val Pro His Met
            675                 680                 685

Ala Pro His His Trp Arg Cys Asp Leu Thr Asn Ala Lys Pro Trp Leu
            690                 695                 700

Leu Ser Glu Thr Asn Asn Asn Met Gly Ala Asn His Thr Leu His Tyr
705                 710                 715                 720
```

-continued

```
Arg Ser Ser Val Gln Phe Trp Leu Asp Glu Lys Ala Ala Leu Ala
            725                 730                 735
Thr Gly Gln Thr Pro Val Cys Tyr Leu Pro Phe Pro Val His Thr Leu
            740                 745                 750
Trp Gln Thr Glu Thr Asp Glu Ile Ser Gly Asn Lys Leu Val Thr
            755                 760             765
Thr Leu Arg Tyr Ala His Gly Ala Trp Asp Gly Arg Glu Arg Glu Phe
770                 775                 780
Arg Gly Phe Gly Tyr Val Glu Gln Thr Asp Ser His Gln Leu Ala Gln
785                 790                 795                 800
Gly Asn Ala Pro Glu Arg Thr Pro Pro Ala Leu Thr Lys Ser Trp Tyr
                    805                 810                 815
Ala Thr Gly Leu Pro Ala Val Asp Asn Ala Leu Ser Ala Gly Tyr Trp
                820                 825                 830
Arg Gly Asp Lys Gln Ala Phe Ala Gly Phe Thr Pro Arg Phe Thr Leu
                835                 840                 845
Trp Lys Glu Gly Lys Asp Val Pro Leu Thr Pro Glu Asp Asp His Asn
850                 855                 860
Leu Tyr Trp Leu Asn Arg Ala Leu Lys Gly Gln Pro Leu Arg Ser Glu
865                 870                 875                 880
Leu Tyr Gly Leu Asp Gly Ser Ala Gln Gln Ile Pro Tyr Thr Val
                    885                 890                 895
Thr Glu Ser Arg Pro Gln Val Arg Gln Leu Gln Asp Gly Ala Thr Val
                900                 905                 910
Ser Pro Val Leu Trp Ala Ser Val Val Glu Ser Arg Ser Tyr His Tyr
                915                 920                 925
Glu Arg Ile Ile Ser Asp Pro Gln Cys Asn Gln Asp Ile Thr Leu Ser
                930                 935                 940
Ser Asp Leu Phe Gly Gln Pro Leu Lys Gln Val Ser Val Gln Tyr Pro
945                 950                 955                 960
Arg Arg Asn Lys Pro Thr Thr Asn Pro Tyr Pro Asp Thr Leu Pro Asp
                    965                 970                 975
Thr Leu Phe Ala Ser Ser Tyr Asp Asp Gln Gln Gln Leu Leu Arg Leu
                980                 985                 990
Thr Cys Arg Gln Ser Ser Trp His His Leu Ile Gly Asn Glu Leu Arg
                995                 1000                1005
Val Leu Gly Leu Pro Asp Gly Thr Arg Ser Asp Ala Phe Thr Tyr
    1010                1015                1020
Asp Ala Lys Gln Val Pro Val Asp Gly Leu Asn Leu Glu Thr Leu
    1025                1030                1035
Cys Ala Glu Asn Ser Leu Ile Ala Asp Asp Lys Pro Arg Glu Tyr
    1040                1045                1050
Leu Asn Gln Gln Arg Thr Phe Tyr Thr Asp Gly Lys Asn Gln Thr
    1055                1060                1065
Pro Leu Lys Thr Pro Thr Arg Gln Ala Leu Ile Ala Phe Thr Glu
    1070                1075                1080
Thr Ala Val Leu Thr Glu Ser Leu Leu Ser Ala Phe Asp Gly Gly
    1085                1090                1095
Ile Thr Pro Asp Glu Leu Pro Gly Ile Leu Thr Gln Ala Gly Tyr
    1100                1105                1110
Gln Gln Glu Pro Tyr Leu Phe Pro Arg Thr Gly Glu Asn Lys Val
    1115                1120                1125
```

-continued

Trp Val Ala Arg Gln Gly Tyr Thr Asp Tyr Gly Thr Glu Ala Gln
1130                1135                1140

Phe Trp Arg Pro Val Ala Gln Arg Asn Ser Leu Leu Thr Gly Lys
1145                1150                1155

Met Thr Leu Lys Trp Asp Thr His Tyr Cys Val Ile Thr Gln Thr
1160                1165                1170

Gln Asp Ala Ala Gly Leu Thr Val Ser Ala Asn Tyr Asp Trp Arg
1175                1180                1185

Phe Leu Thr Pro Thr Gln Leu Thr Asp Ile Asn Asp Asn Val His
1190                1195                1200

Leu Ile Thr Leu Asp Ala Leu Gly Arg Pro Val Thr Gln Arg Phe
1205                1210                1215

Trp Gly Ile Glu Ser Gly Val Ala Thr Gly Tyr Ser Ser Ser Glu
1220                1225                1230

Glu Lys Pro Phe Ser Pro Asn Asp Ile Asp Thr Ala Ile Asn
1235                1240                1245

Leu Thr Gly Pro Leu Pro Val Ala Gln Cys Leu Val Tyr Ala Pro
1250                1255                1260

Asp Ser Trp Met Pro Leu Phe Ser Gln Glu Thr Phe Asn Thr Leu
1265                1270                1275

Thr Gln Glu Glu Gln Glu Thr Leu Arg Asp Ser Arg Ile Ile Thr
1280                1285                1290

Glu Asp Trp Arg Ile Cys Ala Leu Thr Arg Arg Arg Trp Leu Gln
1295                1300                1305

Ser Gln Lys Ile Ser Thr Pro Leu Val Lys Leu Leu Thr Asn Ser
1310                1315                1320

Ile Gly Leu Pro Pro His Asn Leu Thr Leu Thr Thr Asp Arg Tyr
1325                1330                1335

Asp Arg Asp Ser Glu Gln Gln Ile Arg Gln Gln Val Ala Phe Ser
1340                1345                1350

Asp Gly Phe Gly Arg Leu Leu Gln Ala Ser Val Arg His Glu Ala
1355                1360                1365

Gly Glu Ala Trp Gln Arg Asn Gln Asp Gly Ser Leu Val Thr Lys
1370                1375                1380

Val Glu Asn Thr Lys Thr Arg Trp Ala Val Thr Gly Arg Thr Glu
1385                1390                1395

Tyr Asp Asn Lys Gly Gln Thr Ile Arg Thr Tyr Gln Pro Tyr Phe
1400                1405                1410

Leu Asn Asp Trp Arg Tyr Val Ser Asp Ser Ala Arg Lys Glu
1415                1420                1425

Ala Tyr Ala Asp Thr His Ile Tyr Asp Pro Ile Gly Arg Glu Ile
1430                1435                1440

Arg Val Ile Thr Ala Lys Gly Trp Leu Arg Gln Ser Gln Tyr Phe
1445                1450                1455

Pro Trp Phe Thr Val Ser Glu Asp Glu Asn Asp Thr Ala Ala Asp
1460                1465                1470

Ala Leu Val
1475

<210> SEQ ID NO 5
<211> LENGTH: 2745
<212> TYPE: DNA
<213> ORGANISM: Photorhabdus luminescens
<220> FEATURE:
<221> NAME/KEY: CDS -continued

<222> LOCATION: (1)..(2745)

<400> SEQUENCE: 5

| | | | | | | | | | | | | | | | | |
|---|---|---|---|---|---|---|---|---|---|---|---|---|---|---|---|---|
| atg | agc | agt | tac | aat | tct | gca | att | gac | caa | aag | acc | ccc | tcg | att | aag | 48 |
| Met | Ser | Ser | Tyr | Asn | Ser | Ala | Ile | Asp | Gln | Lys | Thr | Pro | Ser | Ile | Lys | |
| 1 | | | | 5 | | | | | 10 | | | | | 15 | | |
| gta | tta | gat | aac | agg | aaa | tta | aat | gta | cgt | act | tta | gaa | tat | cta | cgc | 96 |
| Val | Leu | Asp | Asn | Arg | Lys | Leu | Asn | Val | Arg | Thr | Leu | Glu | Tyr | Leu | Arg | |
| | | | 20 | | | | | 25 | | | | | 30 | | | |
| act | caa | gct | gac | gaa | aac | agt | gat | gaa | tta | att | acg | ttc | tat | gag | ttc | 144 |
| Thr | Gln | Ala | Asp | Glu | Asn | Ser | Asp | Glu | Leu | Ile | Thr | Phe | Tyr | Glu | Phe | |
| | | 35 | | | | | 40 | | | | | 45 | | | | |
| aat | att | ccg | gga | ttt | cag | gta | aaa | agc | acc | gat | cct | cgt | aaa | aat | aaa | 192 |
| Asn | Ile | Pro | Gly | Phe | Gln | Val | Lys | Ser | Thr | Asp | Pro | Arg | Lys | Asn | Lys | |
| | 50 | | | | | 55 | | | | | 60 | | | | | |
| aac | cag | agc | ggc | cca | aat | ttc | att | cgt | gtc | ttt | aat | ctt | gcc | ggt | caa | 240 |
| Asn | Gln | Ser | Gly | Pro | Asn | Phe | Ile | Arg | Val | Phe | Asn | Leu | Ala | Gly | Gln | |
| 65 | | | | | 70 | | | | | 75 | | | | | 80 | |
| gtt | tta | cgt | gaa | gaa | agt | gtt | gat | gcc | ggt | cgg | act | att | acc | ctc | aat | 288 |
| Val | Leu | Arg | Glu | Glu | Ser | Val | Asp | Ala | Gly | Arg | Thr | Ile | Thr | Leu | Asn | |
| | | | | 85 | | | | | 90 | | | | | 95 | | |
| gat | att | gaa | agt | cgc | ccg | gtg | ttg | atc | atc | aat | gca | acc | ggt | gtc | cgc | 336 |
| Asp | Ile | Glu | Ser | Arg | Pro | Val | Leu | Ile | Ile | Asn | Ala | Thr | Gly | Val | Arg | |
| | | | 100 | | | | | 105 | | | | | 110 | | | |
| caa | aac | cat | cgt | tat | gaa | gat | aac | acc | ctt | ccc | ggt | cgt | ctg | ctc | gct | 384 |
| Gln | Asn | His | Arg | Tyr | Glu | Asp | Asn | Thr | Leu | Pro | Gly | Arg | Leu | Leu | Ala | |
| | | 115 | | | | | 120 | | | | | 125 | | | | |
| atc | acc | gaa | caa | gta | cag | gca | gga | gag | aaa | acg | acc | gaa | cgt | ctt | atc | 432 |
| Ile | Thr | Glu | Gln | Val | Gln | Ala | Gly | Glu | Lys | Thr | Thr | Glu | Arg | Leu | Ile | |
| | 130 | | | | | 135 | | | | | 140 | | | | | |
| tgg | gcc | ggc | aat | acg | ccg | caa | gaa | aaa | gat | tac | aac | ctc | gcc | ggt | cag | 480 |
| Trp | Ala | Gly | Asn | Thr | Pro | Gln | Glu | Lys | Asp | Tyr | Asn | Leu | Ala | Gly | Gln | |
| 145 | | | | | 150 | | | | | 155 | | | | | 160 | |
| tgt | gtc | cgc | cat | tac | gat | acc | gcg | gga | ctt | act | caa | ctc | aat | agc | ctt | 528 |
| Cys | Val | Arg | His | Tyr | Asp | Thr | Ala | Gly | Leu | Thr | Gln | Leu | Asn | Ser | Leu | |
| | | | | 165 | | | | | 170 | | | | | 175 | | |
| tct | ctg | gct | ggc | gtc | gtg | cta | tca | caa | tct | caa | caa | ctg | ctt | acc | gat | 576 |
| Ser | Leu | Ala | Gly | Val | Val | Leu | Ser | Gln | Ser | Gln | Gln | Leu | Leu | Thr | Asp | |
| | | | 180 | | | | | 185 | | | | | 190 | | | |
| aac | cag | gat | gcc | gac | tgg | aca | ggt | gaa | gac | cag | agc | ctc | tgg | caa | caa | 624 |
| Asn | Gln | Asp | Ala | Asp | Trp | Thr | Gly | Glu | Asp | Gln | Ser | Leu | Trp | Gln | Gln | |
| | | 195 | | | | | 200 | | | | | 205 | | | | |
| aaa | ctg | agt | agt | gat | gtc | tat | atc | acc | caa | agt | aac | act | gat | gcc | acc | 672 |
| Lys | Leu | Ser | Ser | Asp | Val | Tyr | Ile | Thr | Gln | Ser | Asn | Thr | Asp | Ala | Thr | |
| | 210 | | | | | 215 | | | | | 220 | | | | | |
| ggg | gct | tta | ctg | acc | cag | acc | gat | gcc | aaa | ggc | aac | att | cag | cgg | ctg | 720 |
| Gly | Ala | Leu | Leu | Thr | Gln | Thr | Asp | Ala | Lys | Gly | Asn | Ile | Gln | Arg | Leu | |
| 225 | | | | | 230 | | | | | 235 | | | | | 240 | |
| gcc | tat | gat | gtg | gcc | ggg | cag | cta | aaa | ggg | agt | tgg | tta | aca | ctc | aaa | 768 |
| Ala | Tyr | Asp | Val | Ala | Gly | Gln | Leu | Lys | Gly | Ser | Trp | Leu | Thr | Leu | Lys | |
| | | | | 245 | | | | | 250 | | | | | 255 | | |
| ggt | cag | gcg | gaa | cag | gtg | att | atc | aaa | tcg | cta | acc | tac | tcc | gcc | gcc | 816 |
| Gly | Gln | Ala | Glu | Gln | Val | Ile | Ile | Lys | Ser | Leu | Thr | Tyr | Ser | Ala | Ala | |
| | | | 260 | | | | | 265 | | | | | 270 | | | |
| ggg | caa | aaa | tta | cgt | gaa | gag | cac | ggt | aac | ggg | att | gtc | act | gaa | tac | 864 |
| Gly | Gln | Lys | Leu | Arg | Glu | Glu | His | Gly | Asn | Gly | Ile | Val | Thr | Glu | Tyr | |
| | | 275 | | | | | 280 | | | | | 285 | | | | |
| agc | tac | gaa | ccg | gaa | acc | caa | cgg | ctt | atc | ggc | att | acc | act | cgc | cgt | 912 |
| Ser | Tyr | Glu | Pro | Glu | Thr | Gln | Arg | Leu | Ile | Gly | Ile | Thr | Thr | Arg | Arg | |
| | 290 | | | | | 295 | | | | | 300 | | | | | |

-continued

| | |
|---|---|
| cca tca gac gcc aag gtg ttg caa gac cta cgc tat caa tat gac cca<br>Pro Ser Asp Ala Lys Val Leu Gln Asp Leu Arg Tyr Gln Tyr Asp Pro<br>305                310               315              320 | 960 |
| gta ggc aat gtc att aat atc cgt aat gat gcg gaa gcc act cgc ttt<br>Val Gly Asn Val Ile Asn Ile Arg Asn Asp Ala Glu Ala Thr Arg Phe<br>                 325               330              335 | 1008 |
| tgg cgc aat cag aaa gta gcc ccg gag aat agc tat acc tac gat tcc<br>Trp Arg Asn Gln Lys Val Ala Pro Glu Asn Ser Tyr Thr Tyr Asp Ser<br>        340               345              350 | 1056 |
| ctg tat cag ctt atc agc gcc acc ggg cgc gaa atg gcc aat atc ggt<br>Leu Tyr Gln Leu Ile Ser Ala Thr Gly Arg Glu Met Ala Asn Ile Gly<br>355                360               365 | 1104 |
| cag caa aac aac caa ctt ccc tcc cct gcg cta cct tct gac aac aat<br>Gln Gln Asn Asn Gln Leu Pro Ser Pro Ala Leu Pro Ser Asp Asn Asn<br>    370               375              380 | 1152 |
| acc tac act aac tat act cgc agc tac agc tat gat cac agt ggt aat<br>Thr Tyr Thr Asn Tyr Thr Arg Ser Tyr Ser Tyr Asp His Ser Gly Asn<br>385                390               395              400 | 1200 |
| ctg acg caa att cgg cac agc tcg cca gct acc cag aac aac tac acc<br>Leu Thr Gln Ile Arg His Ser Ser Pro Ala Thr Gln Asn Asn Tyr Thr<br>                 405               410              415 | 1248 |
| gtg gct atc acc ctc tca aac cgc agc aat cgg ggt gtt ctc agt acg<br>Val Ala Ile Thr Leu Ser Asn Arg Ser Asn Arg Gly Val Leu Ser Thr<br>        420               425              430 | 1296 |
| cta acc acc gat cca aat caa gtg gat acg ttg ttt gat gcc ggt ggt<br>Leu Thr Thr Asp Pro Asn Gln Val Asp Thr Leu Phe Asp Ala Gly Gly<br>435                440               445 | 1344 |
| cac caa acc agt tta tta ccc gga cag aca ctt atc tgg aca cca cga<br>His Gln Thr Ser Leu Leu Pro Gly Gln Thr Leu Ile Trp Thr Pro Arg<br>    450               455              460 | 1392 |
| gga gag tta aag cag gtt aat aat ggc ccg gga aat gag tgg tac cgc<br>Gly Glu Leu Lys Gln Val Asn Asn Gly Pro Gly Asn Glu Trp Tyr Arg<br>465                470               475              480 | 1440 |
| tac gac agc aac ggc atg aga caa ctg aaa gtg agt gaa cag cca acc<br>Tyr Asp Ser Asn Gly Met Arg Gln Leu Lys Val Ser Glu Gln Pro Thr<br>                 485               490              495 | 1488 |
| cag aat act acg cag caa caa cgg gta atc tat ttg ccg gga ctg gag<br>Gln Asn Thr Thr Gln Gln Gln Arg Val Ile Tyr Leu Pro Gly Leu Glu<br>        500               505              510 | 1536 |
| cta cgc aca acc cag agc aac gcc aca aca acg gaa gag tta cac gtt<br>Leu Arg Thr Thr Gln Ser Asn Ala Thr Thr Thr Glu Glu Leu His Val<br>515                520               525 | 1584 |
| atc aca ctc ggt gaa gcc ggt cgc gca cag gta cgg gtg ttg cac tgg<br>Ile Thr Leu Gly Glu Ala Gly Arg Ala Gln Val Arg Val Leu His Trp<br>    530               535              540 | 1632 |
| gag agc ggt aag cca gaa gat gtc aac aat aat caa cta cgt tac agc<br>Glu Ser Gly Lys Pro Glu Asp Val Asn Asn Asn Gln Leu Arg Tyr Ser<br>545                550               555              560 | 1680 |
| tac gat aat ctg atc ggc tcc agc cag ctt gaa ctg gac aac caa gga<br>Tyr Asp Asn Leu Ile Gly Ser Ser Gln Leu Glu Leu Asp Asn Gln Gly<br>                 565               570              575 | 1728 |
| caa att atc agc gag gaa gag tat tat cca ttt ggc ggg aca gcg ctg<br>Gln Ile Ile Ser Glu Glu Glu Tyr Tyr Pro Phe Gly Gly Thr Ala Leu<br>        580               585              590 | 1776 |
| tgg gca gca aac agc caa aca gaa gcc agc tat aaa acg att cgc tat<br>Trp Ala Ala Asn Ser Gln Thr Glu Ala Ser Tyr Lys Thr Ile Arg Tyr<br>595                600               605 | 1824 |
| tcc ggc aaa gaa cga gat gcc acc ggg ttg tat tat tac ggt tat cgt<br>Ser Gly Lys Glu Arg Asp Ala Thr Gly Leu Tyr Tyr Tyr Gly Tyr Arg | 1872 |

```
                                                           -continued 610                 615                 620
tat tac caa ccg tgg gcg ggc aga tgg tta agc gcg gac ccg gca gga    1920
Tyr Tyr Gln Pro Trp Ala Gly Arg Trp Leu Ser Ala Asp Pro Ala Gly
625                 630                 635                 640 acc att gat ggg ctg aat cta tac cga atg gta aga aat aat cct gtg    1968
Thr Ile Asp Gly Leu Asn Leu Tyr Arg Met Val Arg Asn Asn Pro Val
                645                 650                 655 agt tta caa gat gaa aat gga tta gcg cca gaa aaa ggg aaa tat acc    2016
Ser Leu Gln Asp Glu Asn Gly Leu Ala Pro Glu Lys Gly Lys Tyr Thr
            660                 665                 670 aaa gag gta aat ttc ttt gat gaa tta aaa ttc aaa ttg gca gcc aaa    2064
Lys Glu Val Asn Phe Phe Asp Glu Leu Lys Phe Lys Leu Ala Ala Lys
        675                 680                 685 agt tca cat gtt gtc aaa tgg aac gag aaa gag agc agt tat aca aaa    2112
Ser Ser His Val Val Lys Trp Asn Glu Lys Glu Ser Ser Tyr Thr Lys
    690                 695                 700 aat aaa tca ttg aaa gtg gtt cgt gtc ggt gat tcc gat ccg tcg ggt    2160
Asn Lys Ser Leu Lys Val Val Arg Val Gly Asp Ser Asp Pro Ser Gly
705                 710                 715                 720 tat ttg cta agc cac gaa gag tta cta aaa ggt ata gaa aaa agt caa    2208
Tyr Leu Leu Ser His Glu Glu Leu Leu Lys Gly Ile Glu Lys Ser Gln
                725                 730                 735 atc ata tat agc cga ctt gaa gaa aac agc tcc ctt tca gaa aaa tca    2256
Ile Ile Tyr Ser Arg Leu Glu Glu Asn Ser Ser Leu Ser Glu Lys Ser
            740                 745                 750 aaa acg aat ctt tct tta gga tct gaa ata tcc ggt tat atg gca aga    2304
Lys Thr Asn Leu Ser Leu Gly Ser Glu Ile Ser Gly Tyr Met Ala Arg
        755                 760                 765 acc ata caa gat acg ata tca gaa tat gcc gaa gag cat aaa tat aga    2352
Thr Ile Gln Asp Thr Ile Ser Glu Tyr Ala Glu Glu His Lys Tyr Arg
    770                 775                 780 agt aat cac cct gat ttt tat tca gaa acc gat ttc ttt gcg tta atg    2400
Ser Asn His Pro Asp Phe Tyr Ser Glu Thr Asp Phe Phe Ala Leu Met
785                 790                 795                 800 gat aaa agt gaa aaa aat gat tat tcc ggt gaa aga aaa att tat gcg    2448
Asp Lys Ser Glu Lys Asn Asp Tyr Ser Gly Glu Arg Lys Ile Tyr Ala
                805                 810                 815 gca atg gag gtt aag gtt tat cat gat tta aaa aat aaa caa tca gaa    2496
Ala Met Glu Val Lys Val Tyr His Asp Leu Lys Asn Lys Gln Ser Glu
            820                 825                 830 tta cat gtc aac tat gca ttg gcc cat ccc tat acg caa ttg agt aat    2544
Leu His Val Asn Tyr Ala Leu Ala His Pro Tyr Thr Gln Leu Ser Asn
        835                 840                 845 gaa gaa aga gcg ctg ttg caa gaa aca gaa ccc gct att gca ata gat    2592
Glu Glu Arg Ala Leu Leu Gln Glu Thr Glu Pro Ala Ile Ala Ile Asp
    850                 855                 860 aga gaa tat aat ttc aaa ggt gtt ggc aaa ttc ctg aca atg aaa gca    2640
Arg Glu Tyr Asn Phe Lys Gly Val Gly Lys Phe Leu Thr Met Lys Ala
865                 870                 875                 880 att aaa aaa tca ttg aaa gga cat aaa att aat agg ata tca aca gag    2688
Ile Lys Lys Ser Leu Lys Gly His Lys Ile Asn Arg Ile Ser Thr Glu
                885                 890                 895 gct att aat att cgc tct gcg gct atc gct gag aat tta gga atg cgg    2736
Ala Ile Asn Ile Arg Ser Ala Ala Ile Ala Glu Asn Leu Gly Met Arg
            900                 905                 910 aga act tca                                                        2745
Arg Thr Ser
        915
```

-continued

<210> SEQ ID NO 6
<211> LENGTH: 915
<212> TYPE: PRT
<213> ORGANISM: Photorhabdus luminescens

<400> SEQUENCE: 6

```
Met Ser Ser Tyr Asn Ser Ala Ile Asp Gln Lys Thr Pro Ser Ile Lys
1               5                   10                  15

Val Leu Asp Asn Arg Lys Leu Asn Val Arg Thr Leu Glu Tyr Leu Arg
            20                  25                  30

Thr Gln Ala Asp Glu Asn Ser Asp Glu Leu Ile Thr Phe Tyr Glu Phe
        35                  40                  45

Asn Ile Pro Gly Phe Gln Val Lys Ser Thr Asp Pro Arg Lys Asn Lys
    50                  55                  60

Asn Gln Ser Gly Pro Asn Phe Ile Arg Val Phe Asn Leu Ala Gly Gln
65                  70                  75                  80

Val Leu Arg Glu Glu Ser Val Asp Ala Gly Arg Thr Ile Thr Leu Asn
                85                  90                  95

Asp Ile Glu Ser Arg Pro Val Leu Ile Ile Asn Ala Thr Gly Val Arg
            100                 105                 110

Gln Asn His Arg Tyr Glu Asp Asn Thr Leu Pro Gly Arg Leu Leu Ala
        115                 120                 125

Ile Thr Glu Gln Val Gln Ala Gly Glu Lys Thr Thr Glu Arg Leu Ile
    130                 135                 140

Trp Ala Gly Asn Thr Pro Gln Glu Lys Asp Tyr Asn Leu Ala Gly Gln
145                 150                 155                 160

Cys Val Arg His Tyr Asp Thr Ala Gly Leu Thr Gln Leu Asn Ser Leu
                165                 170                 175

Ser Leu Ala Gly Val Val Leu Ser Gln Ser Gln Leu Leu Thr Asp
            180                 185                 190

Asn Gln Asp Ala Asp Trp Thr Gly Glu Asp Gln Ser Leu Trp Gln Gln
        195                 200                 205

Lys Leu Ser Ser Asp Val Tyr Ile Thr Gln Ser Asn Thr Asp Ala Thr
    210                 215                 220

Gly Ala Leu Leu Thr Gln Thr Asp Ala Lys Gly Asn Ile Gln Arg Leu
225                 230                 235                 240

Ala Tyr Asp Val Ala Gly Gln Leu Lys Gly Ser Trp Leu Thr Leu Lys
                245                 250                 255

Gly Gln Ala Glu Gln Val Ile Ile Lys Ser Leu Thr Tyr Ser Ala Ala
            260                 265                 270

Gly Gln Lys Leu Arg Glu Glu His Gly Asn Gly Ile Val Thr Glu Tyr
        275                 280                 285

Ser Tyr Glu Pro Glu Thr Gln Arg Leu Ile Gly Ile Thr Thr Arg Arg
    290                 295                 300

Pro Ser Asp Ala Lys Val Leu Gln Asp Leu Arg Tyr Gln Tyr Asp Pro
305                 310                 315                 320

Val Gly Asn Val Ile Asn Ile Arg Asn Asp Ala Glu Ala Thr Arg Phe
                325                 330                 335

Trp Arg Asn Gln Lys Val Ala Pro Glu Asn Ser Tyr Thr Tyr Asp Ser
            340                 345                 350

Leu Tyr Gln Leu Ile Ser Ala Thr Gly Arg Glu Met Ala Asn Ile Gly
        355                 360                 365

Gln Gln Asn Asn Gln Leu Pro Ser Pro Ala Leu Pro Ser Asp Asn Asn
    370                 375                 380
```

-continued

```
Thr Tyr Thr Asn Tyr Thr Arg Ser Tyr Ser Tyr Asp His Ser Gly Asn
385                 390                 395                 400

Leu Thr Gln Ile Arg His Ser Ser Pro Ala Thr Gln Asn Asn Tyr Thr
            405                 410                 415

Val Ala Ile Thr Leu Ser Asn Arg Ser Asn Arg Gly Val Leu Ser Thr
        420                 425                 430

Leu Thr Thr Asp Pro Asn Gln Val Asp Thr Leu Phe Asp Ala Gly Gly
    435                 440                 445

His Gln Thr Ser Leu Leu Pro Gly Gln Thr Leu Ile Trp Thr Pro Arg
450                 455                 460

Gly Glu Leu Lys Gln Val Asn Asn Gly Pro Gly Asn Glu Trp Tyr Arg
465                 470                 475                 480

Tyr Asp Ser Asn Gly Met Arg Gln Leu Lys Val Ser Glu Gln Pro Thr
                485                 490                 495

Gln Asn Thr Thr Gln Gln Arg Val Ile Tyr Leu Pro Gly Leu Glu
            500                 505                 510

Leu Arg Thr Thr Gln Ser Asn Ala Thr Thr Glu Glu Leu His Val
        515                 520                 525

Ile Thr Leu Gly Glu Ala Gly Arg Ala Gln Val Arg Val Leu His Trp
530                 535                 540

Glu Ser Gly Lys Pro Glu Asp Val Asn Asn Asn Gln Leu Arg Tyr Ser
545                 550                 555                 560

Tyr Asp Asn Leu Ile Gly Ser Ser Gln Leu Glu Leu Asp Asn Gln Gly
                565                 570                 575

Gln Ile Ile Ser Glu Glu Glu Tyr Tyr Pro Phe Gly Gly Thr Ala Leu
            580                 585                 590

Trp Ala Ala Asn Ser Gln Thr Glu Ala Ser Tyr Lys Thr Ile Arg Tyr
        595                 600                 605

Ser Gly Lys Glu Arg Asp Ala Thr Gly Leu Tyr Tyr Tyr Gly Tyr Arg
    610                 615                 620

Tyr Tyr Gln Pro Trp Ala Gly Arg Trp Leu Ser Ala Asp Pro Ala Gly
625                 630                 635                 640

Thr Ile Asp Gly Leu Asn Leu Tyr Arg Met Val Arg Asn Asn Pro Val
                645                 650                 655

Ser Leu Gln Asp Glu Asn Gly Leu Ala Pro Glu Lys Gly Lys Tyr Thr
            660                 665                 670

Lys Glu Val Asn Phe Phe Asp Glu Leu Lys Phe Lys Leu Ala Ala Lys
        675                 680                 685

Ser Ser His Val Val Lys Trp Asn Glu Lys Glu Ser Ser Tyr Thr Lys
    690                 695                 700

Asn Lys Ser Leu Lys Val Val Arg Val Gly Asp Ser Asp Pro Ser Gly
705                 710                 715                 720

Tyr Leu Leu Ser His Glu Glu Leu Leu Lys Gly Ile Glu Lys Ser Gln
                725                 730                 735

Ile Ile Tyr Ser Arg Leu Glu Glu Asn Ser Ser Leu Ser Glu Lys Ser
            740                 745                 750

Lys Thr Asn Leu Ser Leu Gly Ser Glu Ile Ser Gly Tyr Met Ala Arg
        755                 760                 765

Thr Ile Gln Asp Thr Ile Ser Glu Tyr Ala Glu His Lys Tyr Arg
    770                 775                 780

Ser Asn His Pro Asp Phe Tyr Ser Glu Thr Asp Phe Phe Ala Leu Met
785                 790                 795                 800

Asp Lys Ser Glu Lys Asn Asp Tyr Ser Gly Glu Arg Lys Ile Tyr Ala
```

-continued

```
                   805                 810                 815
Ala Met Glu Val Lys Val Tyr His Asp Leu Lys Asn Lys Gln Ser Glu
                820                 825                 830

Leu His Val Asn Tyr Ala Leu Ala His Pro Tyr Thr Gln Leu Ser Asn
            835                 840                 845

Glu Glu Arg Ala Leu Leu Gln Glu Thr Glu Pro Ala Ile Ala Ile Asp
        850                 855                 860

Arg Glu Tyr Asn Phe Lys Gly Val Gly Lys Phe Leu Thr Met Lys Ala
865                 870                 875                 880

Ile Lys Lys Ser Leu Lys Gly His Lys Ile Asn Arg Ile Ser Thr Glu
                885                 890                 895

Ala Ile Asn Ile Arg Ser Ala Ala Ile Ala Glu Asn Leu Gly Met Arg
            900                 905                 910

Arg Thr Ser
        915
```

<210> SEQ ID NO 7
<211> LENGTH: 7512
<212> TYPE: DNA
<213> ORGANISM: Photorhabdus luminescens

<400> SEQUENCE: 7

| | | | | | |
|---|---|---|---|---|---|
| atgcaaaact | cattatcaag | cactatcgat | actatttgtc | agaaactgca | attaacttgt | 60 |
| ccggcggaaa | ttgctttgta | tccctttgat | actttccggg | aaaaaactcg | gggaatggtt | 120 |
| aattgggggg | aagcaaaacg | gatttatgaa | attgcacaag | cggaacagga | tagaaaccta | 180 |
| cttcatgaaa | aacgtatttt | tgcctatgct | aatccgctgc | tgaaaaacgc | tgttcggttg | 240 |
| ggtacccggc | aaatgttggg | ttttatacaa | ggttatagtg | atctgtttgg | taatcgtgct | 300 |
| gataactatg | ccgcgccggg | ctcggttgca | tcgatgttct | caccggcggc | ttatttgacg | 360 |
| gaattgtacc | gtgaagccaa | aaacttgcat | gacagcagct | caatttatta | cctagataaa | 420 |
| cgtcgcccgg | atttagcaag | cttaatgctc | agccagaaaa | atatggatga | ggaaatttca | 480 |
| acgctggctc | tctctaatga | attgtgcctt | gccgggatcg | aaacaaaaac | aggaaaatca | 540 |
| caagatgaag | tgatggatat | gttgtcaact | tatcgtttaa | gtggagagac | accttatcat | 600 |
| cacgcttatg | aaactgttcg | tgaaatcgtt | catgaacgtg | atccaggatt | tcgtcatttg | 660 |
| tcacaggcac | ccattgttgc | tgctaagctc | gatcctgtga | ctttgttggg | tattagctcc | 720 |
| catatttcgc | cagaactgta | taacttgctg | attgaggaga | tcccggaaaa | agatgaagcc | 780 |
| gcgcttgata | cgctttataa | aacaaacttt | ggcgatatta | ctactgctca | gttaatgtcc | 840 |
| ccaagttatc | tggcccggta | ttatggcgtc | tcaccggaag | atattgccta | cgtgacgact | 900 |
| tcattatcac | atgttggata | tagcagtgat | attctggtta | ttccgttggt | cgatggtgtg | 960 |
| ggtaagatgg | aagtagttcg | tgttacccga | acaccatcgg | ataattatac | cagtcagacg | 1020 |
| aattatattg | agctgtatcc | acagggtggc | gacaattatt | tgatcaaata | caatctaagc | 1080 |
| aatagttttg | gtttggatga | ttttttatctg | caatataaag | atggttccgc | tgattggact | 1140 |
| gagattgccc | ataatcccta | tcctgatatg | gtcataaatc | aaaagtatga | atcacaggcg | 1200 |
| acaatcaaac | gtagtgactc | tgacaatata | ctcagtatag | ggttacaaag | atggcatagc | 1260 |
| ggtagttata | attttgccgc | cgccaatttt | aaaattgacc | aatactcccc | gaaagctttc | 1320 |
| ctgcttaaaa | tgaataaggc | tattcggttg | ctcaaagcta | ccggcctctc | ttttgctacg | 1380 |
| ttggagcgta | ttgttgatag | tgttaatagc | accaaatcca | tcacggttga | ggtattaaac | 1440 |

-continued

```
aaggtttatc gggtaaaatt ctatattgat cgttatggca tcagtgaaga gacagccgct    1500
attttggcta atattaatat ctctcagcaa gctgttggca atcagcttag ccagtttgag    1560
caactattta atcacccgcc gctcaatggt attcgctatg aaatcagtga ggacaactcc    1620
aaacatcttc ctaatcctga tctgaacctt aaaccagaca gtaccggtga tgatcaacgc    1680
aaggcggttt taaaacgcgc gtttcaggtt aacgccagtg agttgtatca gatgttattg    1740
atcactgatc gtaaagaaga cggtgttatc aaaaataact tagagaattt gtctgatctg    1800
tatttggtta gtttgctggc ccagattcat aacctgacta ttgctgaatt gaacattttg    1860
ttggtgattt gtggctatgg cgacaccaac atttatcaga ttaccgacga taatttagcc    1920
aaaatagtgg aaacattgtt gtggatcact caatggttga agacccaaaa atggacagtt    1980
accgacctgt ttctgatgac cacgccact tacagcacca ctttaacgcc agaaattagc     2040
aatctgacgg ctacgttgtc ttcaactttg catggcaaag agagtctgat tggggaagat    2100
ctgaaaagag caatggcgcc ttgcttcact tcggctttgc atttgacttc tcaagaagtt    2160
gcgtatgacc tgctgttgtg gatagaccag attcaaccgg cacaaataac tgttgatggg    2220
ttttgggaag aagtgcaaac aacaccaacc agcttgaagg tgattacctt tgctcaggtg    2280
ctggcacaat tgagcctgat ctatcgtcgt attgggttaa gtgaaacgga actgtcactg    2340
atcgtgactc aatcttctct gctagtggca ggcaaaagca tactggatca cggtctgtta    2400
accctgatgg ccttggaagg ttttcatacc tgggttaatg gcttggggca acatgcctcc    2460
ttgatattgg cggcgttgaa agacggagcc ttgacagtta ccgatgtagc acaagctatg    2520
aataaggagg aatctctcct acaaatggca gctaatcagg tggagaagga tctaacaaaa    2580
ctgaccagtt ggacacagat tgacgctatt ctgcaatggt tacagatgtc ttcggccttg    2640
gcggtttctc cactggatct ggcagggatg atggccctga aatatgggat agatcataac    2700
tatgctgcct ggcaagctgc ggcggctgcg ctgatggctg atcatgctaa tcaggcacag    2760
aaaaaactgg atgagacgtt cagtaaggca ttatgtaact attatattaa tgctgttgtc    2820
gatagtgctg ctggagtacg tgatcgtaac ggtttatata cctatttgct gattgataat    2880
caggtttctg ccgatgtgat cacttcacgt attgcagaag ctatcgccgg tattcaactg    2940
tacgttaacc gggctttaaa ccgagatgaa ggtcagcttg catcggacgt tagtacccgt    3000
cagttcttca ctgactggga acgttacaat aaacgttaca gtacttgggc tggtgtctct    3060
gaactggtct attatccaga aaactatgtt gatcccactc agcgcattgg gcaaaccaaa    3120
atgatggatg cgctgttgca atccatcaac cagagccagc taaatgcgga tacggtggaa    3180
gatgctttca aaacttattt gaccagcttt gagcaggtag caaatctgaa agtaattagt    3240
gcttaccacg ataatgtgaa tgtggatcaa ggattaactt atttatcgg tatcgaccaa     3300 gcagctccgg gtacgtatta ctggcgtagt gttgatcaca gcaaatgtga aaatggcaag    3360
tttgccgcta atgcttgggg tgagtggaat aaaattacct gtgctgtcaa tccttggaaa    3420
aatatcatcc gtccggttgt ttatatgtcc cgcttatatc tgctatggct ggagcagcaa    3480
tcaaagaaaa gtgatgatgg taaaaccacg atttatcaat ataacttaaa actggctcat    3540
attcgttacg acggtagttg gaatacacca tttactttg atgtgacaga aaaggtaaaa     3600
aattacacgt cgagtactga tgctgctgaa tcttttagggt tgtattgtac tggttatcaa    3660
ggggaagaca ctctattagt tatgttctat tcgatgcaga gtagttatag ctcctatacc    3720
gataataatg cgccggtcac tgggctatat attttcgctg atatgtcatc agacaatatg    3780
acgaatgcac aagcaactaa ctattggaat aacagttatc cgcaatttga tactgtgatg    3840
```

-continued

```
gcagatccgg atagcgacaa taaaaaagtc ataaccagaa gagttaataa ccgttatgcg    3900
gaggattatg aaattccttc ctctgtgaca agtaacagta attattcttg gggtgatcac    3960
agtttaacca tgctttatgg tggtagtgtt cctaatatta cttttgaatc ggcggcagaa    4020
gatttaaggc tatctaccaa tatggcattg agtattattc ataatggata tgcgggaacc    4080
cgccgtatac aatgtaatct tatgaaacaa tacgcttcat taggtgataa atttataatt    4140
tatgattcat catttgatga tgcaaaccgt tttaatctgg tgccattgtt taaattcgga    4200
aaagacgaga actcagatga tagtatttgt atatataatg aaaaccccttc ctctgaagat    4260 aagaagtggt atttttcttc gaaagatgac aataaaacag cggattataa tggtggaact    4320
caatgtatag atgctggaac cagtaacaaa gattttttatt ataatctcca ggagattgaa    4380
gtaattagtg ttactggtgg gtattggtcg agttataaaa tatccaaccc gattaatatc    4440
aatacgggca ttgatagtgc taaagtaaaa gtcaccgtaa aagcgggtgg tgacgatcaa    4500
atctttactg ctgataatag tacctatgtt cctcagcaac cggcacccag ttttgaggag    4560
atgatttatc agttcaataa cctgacaata gattgtaaga atttaaattt catcgacaat    4620
caggcacata ttgagattga tttcaccgct acggcacaag atggccgatt cttgggtgca    4680
gaaactttta ttatcccggt aactaaaaaa gttctcggta ctgagaacgt gattgcgtta    4740
tatagcgaaa ataacggtgt tcaatatatg caaattggcg catatcgtac ccgtttgaat    4800
acgttattcg ctcaacagtt ggttagccgt gctaatcgtg gcattgatgc agtgctcagt    4860
atggaaactc agaatattca ggaaccgcaa ttaggagcgg gcacatatgt gcagcttgtg    4920
ttggataaat atgatgagtc tattcatggc actaataaaa gctttgctat tgaatatgtt    4980
gatatattta aagagaacga tagttttgtg atttatcaag gagaacttag cgaaacaagt    5040
caaactgttg tgaaagtttt cttatcctat tttatagagg cgactggaaa taagaaccac    5100
ttatgggtac gtgctaaata ccaaaaggaa acgactgata agatcttgtt cgaccgtact    5160
gatgagaaag atccgcacgg ttggtttctc agcgacgatc acaagacctt tagtggtctc    5220
tcttccgcac aggcattaaa gaacgacagt gaaccgatgg atttctctgg cgccaatgct    5280
ctctatttct gggaactgtt ctattcacg ccgatgatga tggctcatcg tttgttgcag    5340
gaacagaatt ttgatgcggc gaaccattgg ttccgttatg tctggagtcc atccggttat    5400
atcgttgatg gtaaaattgc tatctaccac tggaacgtgc gaccgctgga agaagacacc    5460
agttggaatg cacaacaact ggactccacc gatccagatg ctgtagccca agatgatccg    5520
atgcactaca aggtggctac ctttatggcg acgttggatc tgctaatggc ccgtggtgat    5580
gctgcttacc gccagttaga gcgtgatacg ttggctgaag ctaaaatgtg gtatacacag    5640
gcgcttaatc tgttgggtga tgagccacaa gtgatgctga gtacgacttg gctaatcca    5700 acattgggta tgctgcttc aaaaaccaca cagcaggttc gtcagcaagt gcttacccag    5760
ttgcgtctca atagcagggt aaaaaacccg ttgctaggaa cagccaattc cctgaccgct    5820
ttattcctgc cgcaggaaaa tagcaagctc aaaggctact ggcggacact ggcgcagcgt    5880
atgtttaatt tacgtcataa tctgtcgatt gacggccagc cgctctcctt gccgctgtat    5940
gctaaaccgg ctgatccaaa agctttactg agtgcggcgg tttcagcttc tcaaggggga    6000
gccgacttgc cgaaggcgcc gctgactatt caccgcttcc ctcaaatgct agaagggca    6060 cggggcttgg ttaaccagct tatacagttc ggtagttcac tattgggta cagtgagcgt    6120 caggatgcgg aagctatgag tcaactactg caaacccaag ccagcgagtt aatactgacc    6180
```

-continued

```
agtattcgta tgcaggataa ccaattggca gagctggatt cggaaaaaac cgccttgcaa    6240
gtctctttag ctggagtgca acaacggttt gacagctata gccaactgta tgaggagaac    6300
atcaacgcag gtgagcagcg agcgctggcg ttacgctcag aatctgctat tgagtctcag    6360
ggagcgcaga tttcccgtat ggcaggcgcg ggtgttgata tggcaccaaa tatcttcggc    6420
ctggctgatg gcggcatgca ttatggtgct attgcctatg ccatcgctga cggtattgag    6480
ttgagtgctt ctgccaagat ggttgatgcg gagaaagttg ctcagtcgga aatatatcgc    6540
cgtcgccgtc aagaatggaa aattcagcgt gacaacgcac aagcggagat taaccagtta    6600
aacgcgcaac tggaatcact gtctattcgc cgtgaagccg ctgaaatgca aaagagtac    6660 ctgaaaaccc agcaagctca ggcgcaggca caacttactt tcttaagaag caaattcagt    6720
aatcaagcgt tatatagttg gttacgaggg cgtttgtcag gtatttattt ccagttctat    6780
gacttggccg tatcacgttg cctgatggca gagcaatcct atcaatggga agctaatgat    6840
aattccatta gctttgtcaa accgggtgca tggcaaggaa cttacgccgg cttattgtgt    6900
ggagaagctt tgatacaaaa tctggcacaa atggaagagg catatctgaa atgggaatct    6960
cgcgctttgg aagtagaacg cacggtttca ttggcagtgg tttatgattc actggaaggt    7020
aatgatcgtt ttaatttagc ggaacaaata cctgcattat tggataaggg ggagggaaca    7080
gcaggaacta aagaaaatgg gttatcattg gctaatgcta tcctgtcagc ttcggtcaaa    7140
ttgtccgact tgaaactggg aacggattat ccagacagta tcgttggtag caacaaggtt    7200
cgtcgtatta agcaaatcag tgtttcgcta cctgcattgg ttgggcctta tcaggatgtt    7260
caggctatgc tcagctatgg tggcagtact caattgccga aaggttgttc agcgttggct    7320
gtgtctcatg gtaccaatga tagtggtcag ttccagttgg atttcaatga cggcaaatac    7380
ctgccatttg aaggtattgc tcttgatgat cagggtacac tgaatcttca atttccgaat    7440
gctaccgaca agcagaaagc aatattgcaa actatgagcg atattatttt gcatattcgt    7500
tataccatcc gt                                                       7512
```

<210> SEQ ID NO 8
<211> LENGTH: 2504
<212> TYPE: PRT
<213> ORGANISM: Photorhabdus luminescens

<400> SEQUENCE: 8

```
Met Gln Asn Ser Leu Ser Ser Thr Ile Asp Thr Ile Cys Gln Lys Leu
1               5                   10                  15

Gln Leu Thr Cys Pro Ala Glu Ile Ala Leu Tyr Pro Phe Asp Thr Phe
            20                  25                  30

Arg Glu Lys Thr Arg Gly Met Val Asn Trp Gly Glu Ala Lys Arg Ile
        35                  40                  45

Tyr Glu Ile Ala Gln Ala Glu Gln Asp Arg Asn Leu Leu His Glu Lys
    50                  55                  60

Arg Ile Phe Ala Tyr Ala Asn Pro Leu Leu Lys Asn Ala Val Arg Leu
65                  70                  75                  80

Gly Thr Arg Gln Met Leu Gly Phe Ile Gln Gly Tyr Ser Asp Leu Phe
                85                  90                  95

Gly Asn Arg Ala Asp Asn Tyr Ala Ala Pro Gly Ser Val Ala Ser Met
            100                 105                 110

Phe Ser Pro Ala Ala Tyr Leu Thr Glu Leu Tyr Arg Glu Ala Lys Asn
        115                 120                 125

Leu His Asp Ser Ser Ser Ile Tyr Tyr Leu Asp Lys Arg Arg Pro Asp
```

```
                130                 135                 140
Leu Ala Ser Leu Met Leu Ser Gln Lys Asn Met Asp Glu Glu Ile Ser
145                 150                 155                 160

Thr Leu Ala Leu Ser Asn Glu Leu Cys Leu Ala Gly Ile Glu Thr Lys
                165                 170                 175

Thr Gly Lys Ser Gln Asp Glu Val Met Asp Met Leu Ser Thr Tyr Arg
                180                 185                 190

Leu Ser Gly Glu Thr Pro Tyr His His Ala Tyr Glu Thr Val Arg Glu
                195                 200                 205

Ile Val His Glu Arg Asp Pro Gly Phe Arg His Leu Ser Gln Ala Pro
210                 215                 220

Ile Val Ala Ala Lys Leu Asp Pro Val Thr Leu Leu Gly Ile Ser Ser
225                 230                 235                 240

His Ile Ser Pro Glu Leu Tyr Asn Leu Leu Ile Glu Glu Ile Pro Glu
                245                 250                 255

Lys Asp Glu Ala Ala Leu Asp Thr Leu Tyr Lys Thr Asn Phe Gly Asp
                260                 265                 270

Ile Thr Thr Ala Gln Leu Met Ser Pro Ser Tyr Leu Ala Arg Tyr Tyr
                275                 280                 285

Gly Val Ser Pro Glu Asp Ile Ala Tyr Val Thr Thr Ser Leu Ser His
                290                 295                 300

Val Gly Tyr Ser Ser Asp Ile Leu Val Ile Pro Leu Val Asp Gly Val
305                 310                 315                 320

Gly Lys Met Glu Val Val Arg Val Thr Arg Thr Pro Ser Asp Asn Tyr
                325                 330                 335

Thr Ser Gln Thr Asn Tyr Ile Glu Leu Tyr Pro Gln Gly Gly Asp Asn
                340                 345                 350

Tyr Leu Ile Lys Tyr Asn Leu Ser Asn Ser Phe Gly Leu Asp Asp Phe
                355                 360                 365

Tyr Leu Gln Tyr Lys Asp Gly Ser Ala Asp Trp Thr Glu Ile Ala His
                370                 375                 380

Asn Pro Tyr Pro Asp Met Val Ile Asn Gln Lys Tyr Glu Ser Gln Ala
385                 390                 395                 400

Thr Ile Lys Arg Ser Asp Ser Asp Asn Ile Leu Ser Ile Gly Leu Gln
                405                 410                 415

Arg Trp His Ser Gly Ser Tyr Asn Phe Ala Ala Asn Phe Lys Ile
                420                 425                 430

Asp Gln Tyr Ser Pro Lys Ala Phe Leu Leu Lys Met Asn Lys Ala Ile
                435                 440                 445

Arg Leu Leu Lys Ala Thr Gly Leu Ser Phe Ala Thr Leu Glu Arg Ile
450                 455                 460

Val Asp Ser Val Asn Ser Thr Lys Ser Ile Thr Val Glu Val Leu Asn
465                 470                 475                 480

Lys Val Tyr Arg Val Lys Phe Tyr Ile Asp Arg Tyr Gly Ile Ser Glu
                485                 490                 495

Glu Thr Ala Ala Ile Leu Ala Asn Ile Asn Ile Ser Gln Gln Ala Val
                500                 505                 510

Gly Asn Gln Leu Ser Gln Phe Glu Gln Leu Phe Asn His Pro Pro Leu
                515                 520                 525

Asn Gly Ile Arg Tyr Glu Ile Ser Glu Asp Asn Ser Lys His Leu Pro
                530                 535                 540

Asn Pro Asp Leu Asn Leu Lys Pro Asp Ser Thr Gly Asp Asp Gln Arg
545                 550                 555                 560
```

-continued

```
Lys Ala Val Leu Lys Arg Ala Phe Gln Val Asn Ala Ser Glu Leu Tyr
            565                 570                 575
Gln Met Leu Leu Ile Thr Asp Arg Lys Glu Asp Gly Val Ile Lys Asn
        580                 585                 590
Asn Leu Glu Asn Leu Ser Asp Leu Tyr Leu Val Ser Leu Leu Ala Gln
    595                 600                 605
Ile His Asn Leu Thr Ile Ala Glu Leu Asn Ile Leu Val Ile Cys
610                 615                 620
Gly Tyr Gly Asp Thr Asn Ile Tyr Gln Ile Thr Asp Asp Asn Leu Ala
625                 630                 635                 640
Lys Ile Val Glu Thr Leu Leu Trp Ile Thr Gln Trp Leu Lys Thr Gln
            645                 650                 655
Lys Trp Thr Val Thr Asp Leu Phe Leu Met Thr Thr Ala Thr Tyr Ser
        660                 665                 670
Thr Thr Leu Thr Pro Glu Ile Ser Asn Leu Thr Ala Thr Leu Ser Ser
    675                 680                 685
Thr Leu His Gly Lys Glu Ser Leu Ile Gly Glu Asp Leu Lys Arg Ala
690                 695                 700
Met Ala Pro Cys Phe Thr Ser Ala Leu His Leu Thr Ser Gln Glu Val
705                 710                 715                 720
Ala Tyr Asp Leu Leu Trp Ile Asp Gln Ile Gln Pro Ala Gln Ile
            725                 730                 735
Thr Val Asp Gly Phe Trp Glu Glu Val Gln Thr Thr Pro Thr Ser Leu
        740                 745                 750
Lys Val Ile Thr Phe Ala Gln Val Leu Ala Gln Leu Ser Leu Ile Tyr
    755                 760                 765
Arg Arg Ile Gly Leu Ser Glu Thr Glu Leu Ser Leu Ile Val Thr Gln
770                 775                 780
Ser Ser Leu Leu Val Ala Gly Lys Ser Ile Leu Asp His Gly Leu Leu
785                 790                 795                 800
Thr Leu Met Ala Leu Glu Gly Phe His Thr Trp Val Asn Gly Leu Gly
            805                 810                 815
Gln His Ala Ser Leu Ile Leu Ala Ala Leu Lys Asp Gly Ala Leu Thr
        820                 825                 830
Val Thr Asp Val Ala Gln Ala Met Asn Lys Glu Glu Ser Leu Leu Gln
    835                 840                 845
Met Ala Ala Asn Gln Val Glu Lys Asp Leu Thr Lys Leu Thr Ser Trp
850                 855                 860
Thr Gln Ile Asp Ala Ile Leu Gln Trp Leu Gln Met Ser Ser Ala Leu
865                 870                 875                 880
Ala Val Ser Pro Leu Asp Leu Ala Gly Met Met Ala Leu Lys Tyr Gly
            885                 890                 895
Ile Asp His Asn Tyr Ala Ala Trp Gln Ala Ala Ala Ala Leu Met
        900                 905                 910
Ala Asp His Ala Asn Gln Ala Gln Lys Lys Leu Asp Glu Thr Phe Ser
    915                 920                 925
Lys Ala Leu Cys Asn Tyr Tyr Ile Asn Ala Val Val Asp Ser Ala Ala
930                 935                 940
Gly Val Arg Asp Arg Asn Gly Leu Tyr Thr Tyr Leu Leu Ile Asp Asn
945                 950                 955                 960
Gln Val Ser Ala Asp Val Ile Thr Ser Arg Ile Ala Glu Ala Ile Ala
            965                 970                 975
```

-continued

```
Gly Ile Gln Leu Tyr Val Asn Arg Ala Leu Asn Arg Asp Glu Gly Gln
            980                 985                 990
Leu Ala Ser Asp Val Ser Thr Arg Gln Phe Phe Thr Asp Trp Glu Arg
        995                 1000                1005
Tyr Asn Lys Arg Tyr Ser Thr Trp Ala Gly Val Ser Glu Leu Val
    1010                1015                1020
Tyr Tyr Pro Glu Asn Tyr Val Asp Pro Thr Gln Arg Ile Gly Gln
    1025                1030                1035
Thr Lys Met Met Asp Ala Leu Leu Gln Ser Ile Asn Gln Ser Gln
    1040                1045                1050
Leu Asn Ala Asp Thr Val Glu Asp Ala Phe Lys Thr Tyr Leu Thr
    1055                1060                1065
Ser Phe Glu Gln Val Ala Asn Leu Lys Val Ile Ser Ala Tyr His
    1070                1075                1080
Asp Asn Val Asn Val Asp Gln Gly Leu Thr Tyr Phe Ile Gly Ile
    1085                1090                1095
Asp Gln Ala Ala Pro Gly Thr Tyr Tyr Trp Arg Ser Val Asp His
    1100                1105                1110
Ser Lys Cys Glu Asn Gly Lys Phe Ala Ala Asn Ala Trp Gly Glu
    1115                1120                1125
Trp Asn Lys Ile Thr Cys Ala Val Asn Pro Trp Lys Asn Ile Ile
    1130                1135                1140
Arg Pro Val Val Tyr Met Ser Arg Leu Tyr Leu Leu Trp Leu Glu
    1145                1150                1155
Gln Gln Ser Lys Lys Ser Asp Asp Gly Lys Thr Thr Ile Tyr Gln
    1160                1165                1170
Tyr Asn Leu Lys Leu Ala His Ile Arg Tyr Asp Gly Ser Trp Asn
    1175                1180                1185
Thr Pro Phe Thr Phe Asp Val Thr Glu Lys Val Lys Asn Tyr Thr
    1190                1195                1200
Ser Ser Thr Asp Ala Ala Glu Ser Leu Gly Leu Tyr Cys Thr Gly
    1205                1210                1215
Tyr Gln Gly Glu Asp Thr Leu Leu Val Met Phe Tyr Ser Met Gln
    1220                1225                1230
Ser Ser Tyr Ser Ser Tyr Thr Asp Asn Asn Ala Pro Val Thr Gly
    1235                1240                1245
Leu Tyr Ile Phe Ala Asp Met Ser Ser Asp Asn Met Thr Asn Ala
    1250                1255                1260
Gln Ala Thr Asn Tyr Trp Asn Asn Ser Tyr Pro Gln Phe Asp Thr
    1265                1270                1275
Val Met Ala Asp Pro Asp Ser Asp Asn Lys Lys Val Ile Thr Arg
    1280                1285                1290
Arg Val Asn Asn Arg Tyr Ala Glu Asp Tyr Glu Ile Pro Ser Ser
    1295                1300                1305
Val Thr Ser Asn Ser Asn Tyr Ser Trp Gly Asp His Ser Leu Thr
    1310                1315                1320
Met Leu Tyr Gly Gly Ser Val Pro Asn Ile Thr Phe Glu Ser Ala
    1325                1330                1335
Ala Glu Asp Leu Arg Leu Ser Thr Asn Met Ala Leu Ser Ile Ile
    1340                1345                1350
His Asn Gly Tyr Ala Gly Thr Arg Arg Ile Gln Cys Asn Leu Met
    1355                1360                1365
Lys Gln Tyr Ala Ser Leu Gly Asp Lys Phe Ile Ile Tyr Asp Ser
```

```
                        1370               1375              1380
Ser Phe Asp Asp Ala Asn Arg Phe Asn Leu Val Pro Leu Phe Lys
    1385              1390              1395
Phe Gly Lys Asp Glu Asn Ser Asp Asp Ser Ile Cys Ile Tyr Asn
    1400              1405              1410
Glu Asn Pro Ser Ser Glu Asp Lys Lys Trp Tyr Phe Ser Ser Lys
    1415              1420              1425
Asp Asp Asn Lys Thr Ala Asp Tyr Asn Gly Gly Thr Gln Cys Ile
    1430              1435              1440
Asp Ala Gly Thr Ser Asn Lys Asp Phe Tyr Tyr Asn Leu Gln Glu
    1445              1450              1455
Ile Glu Val Ile Ser Val Thr Gly Gly Tyr Trp Ser Ser Tyr Lys
    1460              1465              1470
Ile Ser Asn Pro Ile Asn Ile Asn Thr Gly Ile Asp Ser Ala Lys
    1475              1480              1485
Val Lys Val Thr Val Lys Ala Gly Gly Asp Asp Gln Ile Phe Thr
    1490              1495              1500
Ala Asp Asn Ser Thr Tyr Val Pro Gln Gln Pro Ala Pro Ser Phe
    1505              1510              1515
Glu Glu Met Ile Tyr Gln Phe Asn Asn Leu Thr Ile Asp Cys Lys
    1520              1525              1530
Asn Leu Asn Phe Ile Asp Asn Gln Ala His Ile Glu Ile Asp Phe
    1535              1540              1545
Thr Ala Thr Ala Gln Asp Gly Arg Phe Leu Gly Ala Glu Thr Phe
    1550              1555              1560
Ile Ile Pro Val Thr Lys Lys Val Leu Gly Thr Glu Asn Val Ile
    1565              1570              1575
Ala Leu Tyr Ser Glu Asn Asn Gly Val Gln Tyr Met Gln Ile Gly
    1580              1585              1590
Ala Tyr Arg Thr Arg Leu Asn Thr Leu Phe Ala Gln Gln Leu Val
    1595              1600              1605
Ser Arg Ala Asn Arg Gly Ile Asp Ala Val Leu Ser Met Glu Thr
    1610              1615              1620
Gln Asn Ile Gln Glu Pro Gln Leu Gly Ala Gly Thr Tyr Val Gln
    1625              1630              1635
Leu Val Leu Asp Lys Tyr Asp Glu Ser Ile His Gly Thr Asn Lys
    1640              1645              1650
Ser Phe Ala Ile Glu Tyr Val Asp Ile Phe Lys Glu Asn Asp Ser
    1655              1660              1665
Phe Val Ile Tyr Gln Gly Glu Leu Ser Glu Thr Ser Gln Thr Val
    1670              1675              1680
Val Lys Val Phe Leu Ser Tyr Phe Ile Glu Ala Thr Gly Asn Lys
    1685              1690              1695
Asn His Leu Trp Val Arg Ala Lys Tyr Gln Lys Glu Thr Thr Asp
    1700              1705              1710
Lys Ile Leu Phe Asp Arg Thr Asp Glu Lys Asp Pro His Gly Trp
    1715              1720              1725
Phe Leu Ser Asp Asp His Lys Thr Phe Ser Gly Leu Ser Ser Ala
    1730              1735              1740
Gln Ala Leu Lys Asn Asp Ser Glu Pro Met Asp Phe Ser Gly Ala
    1745              1750              1755
Asn Ala Leu Tyr Phe Trp Glu Leu Phe Tyr Tyr Thr Pro Met Met
    1760              1765              1770
```

-continued

```
Met Ala His Arg Leu Leu Gln Glu Gln Asn Phe Asp Ala Ala Asn
1775                1780                1785

His Trp Phe Arg Tyr Val Trp Ser Pro Ser Gly Tyr Ile Val Asp
1790                1795                1800

Gly Lys Ile Ala Ile Tyr His Trp Asn Val Arg Pro Leu Glu Glu
1805                1810                1815

Asp Thr Ser Trp Asn Ala Gln Gln Leu Asp Ser Thr Asp Pro Asp
1820                1825                1830

Ala Val Ala Gln Asp Asp Pro Met His Tyr Lys Val Ala Thr Phe
1835                1840                1845

Met Ala Thr Leu Asp Leu Leu Met Ala Arg Gly Asp Ala Ala Tyr
1850                1855                1860

Arg Gln Leu Glu Arg Asp Thr Leu Ala Glu Ala Lys Met Trp Tyr
1865                1870                1875

Thr Gln Ala Leu Asn Leu Leu Gly Asp Glu Pro Gln Val Met Leu
1880                1885                1890

Ser Thr Thr Trp Ala Asn Pro Thr Leu Gly Asn Ala Ala Ser Lys
1895                1900                1905

Thr Thr Gln Gln Val Arg Gln Val Leu Thr Gln Leu Arg Leu
1910                1915                1920

Asn Ser Arg Val Lys Thr Pro Leu Leu Gly Thr Ala Asn Ser Leu
1925                1930                1935

Thr Ala Leu Phe Leu Pro Gln Glu Asn Ser Lys Leu Lys Gly Tyr
1940                1945                1950

Trp Arg Thr Leu Ala Gln Arg Met Phe Asn Leu Arg His Asn Leu
1955                1960                1965

Ser Ile Asp Gly Gln Pro Leu Ser Leu Pro Leu Tyr Ala Lys Pro
1970                1975                1980

Ala Asp Pro Lys Ala Leu Leu Ser Ala Ala Val Ser Ala Ser Gln
1985                1990                1995

Gly Gly Ala Asp Leu Pro Lys Ala Pro Leu Thr Ile His Arg Phe
2000                2005                2010

Pro Gln Met Leu Glu Gly Ala Arg Gly Leu Val Asn Gln Leu Ile
2015                2020                2025

Gln Phe Gly Ser Ser Leu Leu Gly Tyr Ser Glu Arg Gln Asp Ala
2030                2035                2040

Glu Ala Met Ser Gln Leu Leu Gln Thr Gln Ala Ser Glu Leu Ile
2045                2050                2055

Leu Thr Ser Ile Arg Met Gln Asp Asn Gln Leu Ala Glu Leu Asp
2060                2065                2070

Ser Glu Lys Thr Ala Leu Gln Val Ser Leu Ala Gly Val Gln Gln
2075                2080                2085

Arg Phe Asp Ser Tyr Ser Gln Leu Tyr Glu Glu Asn Ile Asn Ala
2090                2095                2100

Gly Glu Gln Arg Ala Leu Ala Leu Arg Ser Glu Ser Ala Ile Glu
2105                2110                2115

Ser Gln Gly Ala Gln Ile Ser Arg Met Ala Gly Ala Gly Val Asp
2120                2125                2130

Met Ala Pro Asn Ile Phe Gly Leu Ala Asp Gly Gly Met His Tyr
2135                2140                2145

Gly Ala Ile Ala Tyr Ala Ile Ala Asp Gly Ile Glu Leu Ser Ala
2150                2155                2160
```

-continued

```
Ser Ala Lys Met Val Asp Ala Glu Lys Val Ala Gln Ser Glu Ile
2165                2170                2175

Tyr Arg Arg Arg Arg Gln Glu Trp Lys Ile Gln Arg Asp Asn Ala
2180                2185                2190

Gln Ala Glu Ile Asn Gln Leu Asn Ala Gln Leu Glu Ser Leu Ser
2195                2200                2205

Ile Arg Arg Glu Ala Ala Glu Met Gln Lys Glu Tyr Leu Lys Thr
2210                2215                2220

Gln Gln Ala Gln Ala Gln Ala Gln Leu Thr Phe Leu Arg Ser Lys
2225                2230                2235

Phe Ser Asn Gln Ala Leu Tyr Ser Trp Leu Arg Gly Arg Leu Ser
2240                2245                2250

Gly Ile Tyr Phe Gln Phe Tyr Asp Leu Ala Val Ser Arg Cys Leu
2255                2260                2265

Met Ala Glu Gln Ser Tyr Gln Trp Glu Ala Asn Asp Asn Ser Ile
2270                2275                2280

Ser Phe Val Lys Pro Gly Ala Trp Gln Gly Thr Tyr Ala Gly Leu
2285                2290                2295

Leu Cys Gly Glu Ala Leu Ile Gln Asn Leu Ala Gln Met Glu Glu
2300                2305                2310

Ala Tyr Leu Lys Trp Glu Ser Arg Ala Leu Glu Val Glu Arg Thr
2315                2320                2325

Val Ser Leu Ala Val Val Tyr Asp Ser Leu Glu Gly Asn Asp Arg
2330                2335                2340

Phe Asn Leu Ala Glu Gln Ile Pro Ala Leu Leu Asp Lys Gly Glu
2345                2350                2355

Gly Thr Ala Gly Thr Lys Glu Asn Gly Leu Ser Leu Ala Asn Ala
2360                2365                2370

Ile Leu Ser Ala Ser Val Lys Leu Ser Asp Leu Lys Leu Gly Thr
2375                2380                2385

Asp Tyr Pro Asp Ser Ile Val Gly Ser Asn Lys Val Arg Arg Ile
2390                2395                2400

Lys Gln Ile Ser Val Ser Leu Pro Ala Leu Val Gly Pro Tyr Gln
2405                2410                2415

Asp Val Gln Ala Met Leu Ser Tyr Gly Gly Ser Thr Gln Leu Pro
2420                2425                2430

Lys Gly Cys Ser Ala Leu Ala Val Ser His Gly Thr Asn Asp Ser
2435                2440                2445

Gly Gln Phe Gln Leu Asp Phe Asn Asp Gly Lys Tyr Leu Pro Phe
2450                2455                2460

Glu Gly Ile Ala Leu Asp Asp Gln Gly Thr Leu Asn Leu Gln Phe
2465                2470                2475

Pro Asn Ala Thr Asp Lys Gln Lys Ala Ile Leu Gln Thr Met Ser
2480                2485                2490

Asp Ile Ile Leu His Ile Arg Tyr Thr Ile Arg
2495                2500
```